(12) United States Patent
Bouhnik et al.

(10) Patent No.: US 11,607,190 B2
(45) Date of Patent: Mar. 21, 2023

(54) SYSTEMS AND METHODS FOR DYNAMIC SCANNING WITH MULTI-HEAD CAMERA

(71) Applicant: General Electric Company, Schenectady, NY (US)

(72) Inventors: Jean-Paul Bouhnik, Tirat Carmel (IL); Yaron Hefetz, Tirat Carmel (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 12 days.

(21) Appl. No.: 17/176,615

(22) Filed: Feb. 16, 2021

(65) Prior Publication Data

US 2021/0161500 A1 Jun. 3, 2021

Related U.S. Application Data

(63) Continuation of application No. 15/282,521, filed on Sep. 30, 2016, now Pat. No. 10,932,746, which is a continuation-in-part of application No. 14/788,180, filed on Jun. 30, 2015, now Pat. No. 10,143,437.

(51) Int. Cl.
| | |
|---|---|
| *A61B 6/00* | (2006.01) |
| *A61B 6/03* | (2006.01) |
| *A61B 6/06* | (2006.01) |

(52) U.S. Cl.
CPC .............. *A61B 6/545* (2013.01); *A61B 6/037* (2013.01); *A61B 6/4266* (2013.01); *A61B 6/4429* (2013.01); *A61B 6/52* (2013.01); *A61B 6/5205* (2013.01); *A61B 6/547* (2013.01); *A61B 6/032* (2013.01); *A61B 6/06* (2013.01); *A61B 6/44* (2013.01); *A61B 6/4417* (2013.01)

(58) Field of Classification Search
None
See application file for complete search history.

(56) References Cited

U.S. PATENT DOCUMENTS

| | | | | |
|---|---|---|---|---|
| 6,748,044 | B2 * | 6/2004 | Sabol | G06T 7/0012 |
| | | | | 250/363.04 |
| 7,283,606 | B2 * | 10/2007 | Kalender | G06T 11/006 |
| | | | | 378/15 |
| 8,492,725 | B2 * | 7/2013 | Zilberstein | A61B 6/04 |
| | | | | 250/363.04 |
| 2010/0046817 | A1 * | 2/2010 | Goedicke | G01T 1/17 |
| | | | | 378/62 |
| 2015/0119704 | A1 * | 4/2015 | Roth | A61B 6/4258 |
| | | | | 600/425 |

* cited by examiner

*Primary Examiner* — Angela M Hoffa
*Assistant Examiner* — Younhee Choi

(57) ABSTRACT

A nuclear medicine (NM) multi-head imaging system is provided that includes a gantry, plural detector units mounted to the gantry, and at least one processor operably coupled to at least one of the detector units. The detector units are mounted to the gantry. Each detector unit defines a detector unit position and corresponding view oriented toward a center of the bore. Each detector unit is configured to acquire imaging information over a sweep range corresponding to the corresponding view. The at least one processor is configured to, for each detector unit, determine plural angular positions along the sweep range corresponding to boundaries of the object to be imaged, generate a representation of each angular position for each detector unit position, generate a model based on the angular positions using the representation, and determine scan parameters to be used to image the object using the model.

17 Claims, 16 Drawing Sheets

SYSTEMS AND METHODS FOR DYNAMIC SCANNING WITH MULTI-HEAD CAMERA

RELATED APPLICATIONS

The present application claims priority to and is a continuation of U.S. patent application Ser. No. 15/282,521, entitled "Systems and Methods for Dynamic Scanning with Multi-Head Camera," filed Sep. 30, 2016, which is a continuation-in-part of U.S. patent application Ser. No. 14/788,180, filed Jun. 30, 2015, which has issued as U.S. Pat. No. 10,143,437, entitled "Systems and Methods for Dynamic Scanning with Multi-Head Camera." The entire disclosures of U.S. patent application Ser. No. 15/282,521 and U.S. patent application Ser. No. 14/788,180 are incorporated herein by reference.

BACKGROUND

The subject matter disclosed herein relates generally to medical imaging systems, and more particularly to radiation detection systems.

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

An NM imaging system may be configured as a multi-head imaging system having a number of individual detectors distributed about the gantry. Each detector may pivot or sweep to provide a range over which the detector may acquire information that is larger than a stationary field of view of the detector. However, as a detector sweeps through a range, the detector may acquire imaging information that is not of interest, or not as useful as information from a region of interest that is covered by only a portion of a range. The time spent by the detector collecting information that is not of interest may result in an inefficient acquisition time.

BRIEF DESCRIPTION

In accordance with an embodiment, a nuclear medicine (NM) multi-head imaging system is provided that includes a gantry, plural detector units mounted to the gantry, and at least one processor operably coupled to at least one of the detector units. The gantry defines a bore configured to accept an object to be imaged. The detector units are mounted to the gantry, with each detector unit defining a detector unit position and corresponding view oriented toward a center of the bore. Each detector unit is configured to acquire imaging information over a sweep range corresponding to the corresponding view. The at least one processor is configured to, for each detector unit, determine plural angular positions along the sweep range corresponding to boundaries of the object to be imaged, generate a representation of each angular position for each detector unit position (e.g., a plot for each angular position for each detector unit position), generate a model based on the angular positions using the representation (e.g., generate an angular positional curve for each angular position using the plot), and determine scan parameters to be used to image the object using the model (e.g., using the angular positional curves).

In accordance with another embodiment, a method includes determining, for each detector unit of an imaging system distributed about a bore of a gantry, plural angular positions along a corresponding sweep range. The method also includes generating a representation of each angular position for each detector unit position (e.g., a plot for each angular position for each detector unit position), and generating a model based on the angular positions using the representation (e.g., generate an angular positional curve for each angular position using the plot). Also, the method includes determining scan parameters to be used to image the object using the model (e.g., using the angular positional curves). Further, the method includes acquiring imaging information using the determined scan parameters. The method also includes reconstructing an image using the imaging information.

In accordance with another embodiment, a method includes determining a regularly shaped footprint that surrounds an irregular shape of an object to be imaged. The method also includes advancing at least some of a group of detector units distributed about a bore of a gantry to the regularly shaped footprint. Further, the method includes acquiring imaging information with the at least some of the detector units positioned at the regularly shaped footprint.

DETAILED DESCRIPTION

Figure 1:
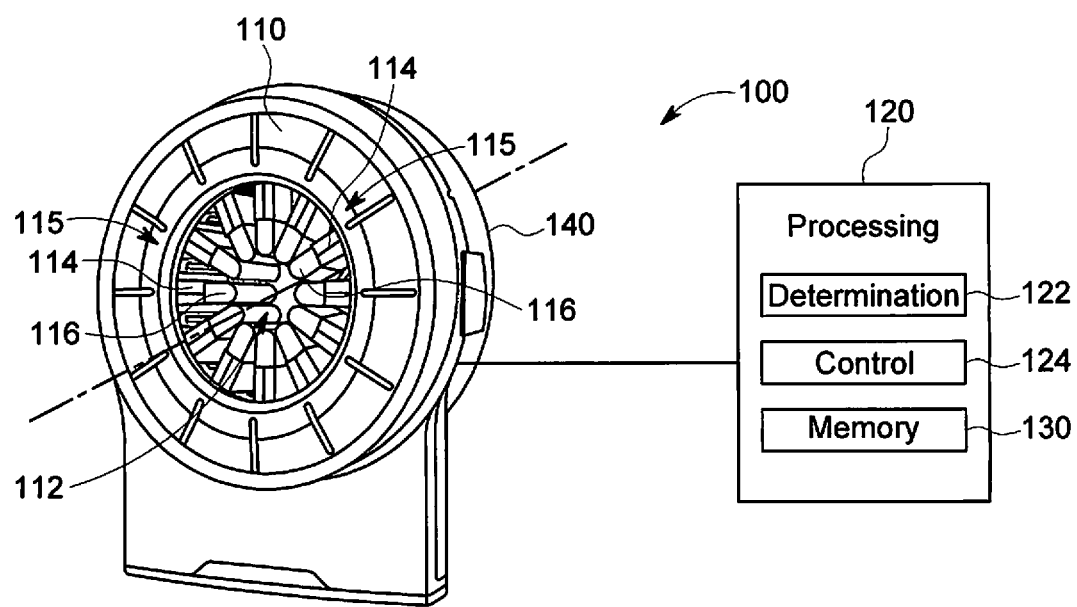
FIG. 1 provides a schematic view of a nuclear medicine (NM) imaging system according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for reducing acquisition time and/or improving image quality for NM imaging systems including at least one detector that sweeps over a range during image acquisition.

For example, in some embodiments, detectors of a multi-head camera begin scanning a patient with the heads of the detectors at an extreme view angle (e.g., at an edge or boundary of a sweep range). It may be noted that in other embodiments the detector heads may begin at other positions, which may be different for each detector head. During the first cycle or sweep of the detectors over a range, a processor receiving information (e.g., photon counts) from the detectors monitors the received information. When the activity (e.g., photon counts) corresponding to a region of interest of the patient comes into view of a sweeping detector, the processor dynamically marks the view angle as a start of an acquisition range. The heads continue to pivot and the processor continues to monitor collected information. When the activity comes out of view, the processor dynamically marks the corresponding view angle as the end of the acquisition range. The pivot direction may then be reversed and the head scans from the end of the acquisition range to the start of the range. In some embodiments, the pivot direction may be reversed again and the head scans from the start of the range to the end of the range. The process may repeat a number of times until a desired amount of imaging information has been collected.

In some embodiments, a user may input at least one numerical patient parameter, such as one or more of weight, head radius, head circumference, body mass index, or the like. Additionally or alternatively, at least one numerical patient parameter may be accessed from a patient file. A processor of the imaging system may then calculate a patient adapted initial starting point for the scan based on the one or more numerical patient parameters.

A technical effect of at least one embodiment includes improved image quality. A technical effect of at least one embodiment includes reduced acquisition time.

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical. The depicted imaging system 100 includes a gantry 110 and a processing unit 120.

The gantry 100 defines a bore 112. The bore 112 is configured to accept an object to be imaged (e.g., a human patient or portion thereof). As seen in FIG. 1, plural detector units 115 are mounted to the gantry 110. In the illustrated embodiment, each detector unit 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector.

The volumes of the detector under the pixelated anodes are defined as voxels (not shown). For each pixelated anode, the detector has a corresponding voxel. The absorption of photons by certain voxels corresponding to particular pixelated anodes results in charges generated that may be counted. The counts may be correlated to particular locations and used to reconstruct an image.

Figure 2:
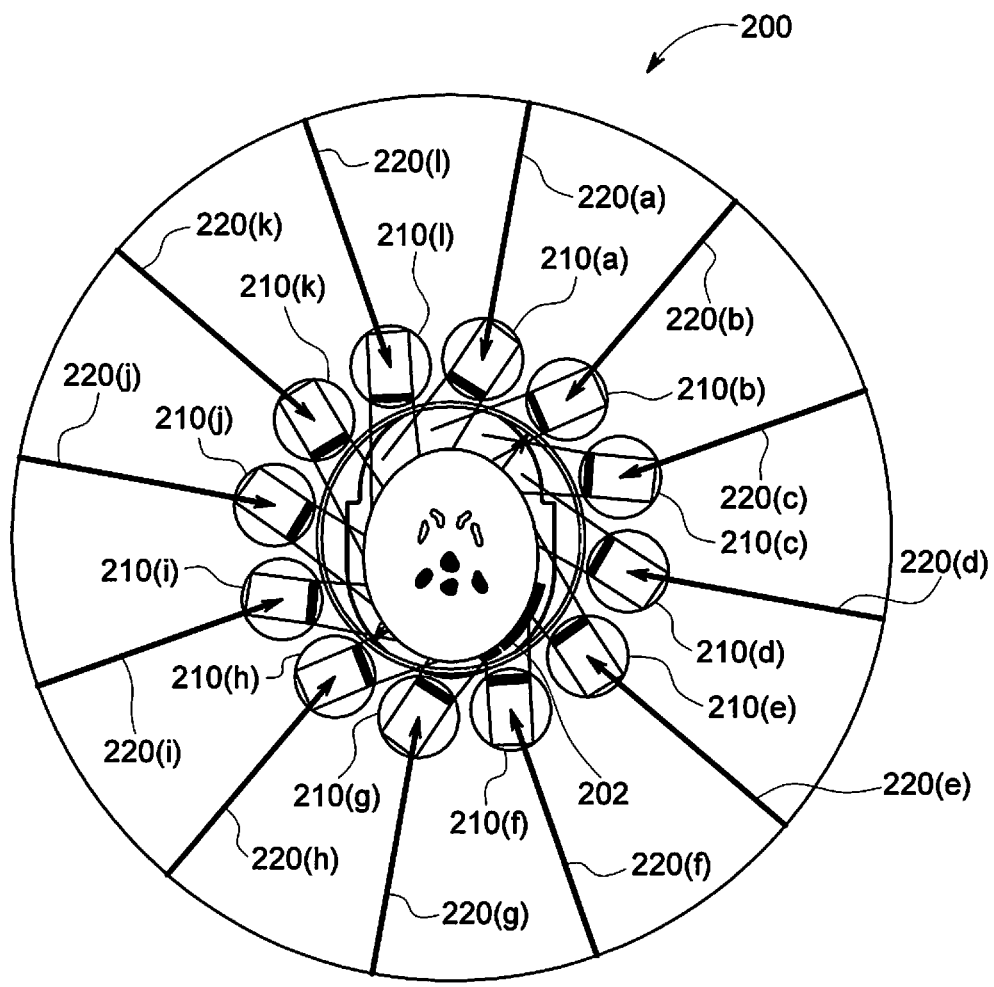
FIG. 2 provides a schematic view of a detector arrangement according to an embodiment.

In various embodiments, each detector unit 115 may define a corresponding view that is oriented toward the center of the bore 112. Each detector unit 115 in the illustrated embodiment is configured to acquire imaging information over a sweep range corresponding to the view of the given detector unit. FIG. 2 illustrates a detector arrangement 200 in accordance with various embodiments. The detector units of FIG. 1, for example, may be arranged in accordance with aspects of the detector arrangement 200. In some embodiments, the system 100 further includes a CT (computed tomography) detection unit 140. The CT detection unit 140 may be centered about the bore 112. Images acquired using both NM and CT by the system are accordingly naturally registered by the fact that the NM and CT detection units are positioned relative to each other in a known relationship. A patient may be imaged using both CT and NM modalities at the same imaging session, while remaining on the same bed, which may transport the patient along the common NM-CT bore 112.

As seen in FIG. 2, the detector arrangement 200 includes detector units 210(a), 210(b), 210(c), 210(d), 210(e), 210(f), 210(g), 210(h), 210(i), 210(j), 210(k), 210(l) disposed about and oriented toward (e.g., a detection or acquisition surface of the detector units, and/or the collimator's FOV (Field Of View), are oriented toward) an object 202 to be imaged in the center of a bore. Each detector unit of the illustrated embodiment defines a corresponding view that may be oriented toward the center of the bore of the detector arrangement 200. The view for each detector unit 210, for example, may be aligned along a central axis of a corresponding arm (e.g., arm 114) of the detector unit 210. In the illustrated embodiment, the detector unit 210(A) defines a corresponding view 220(A), the detector unit 210(B) defines a corresponding view 220(B), the detector unit 210(C) defines a corresponding view 220(C), and so on. The detector units 210 are configured to sweep or pivot (thus sweeping the corresponding FOV's) over a sweep range (or portion thereof) bounded on either side of a line defined by the corresponding view during acquisition of imaging information. Thus, each detector unit 210 may collect information over a range larger than a field of view defined by a stationary detector unit. It may be noted that, generally, the sweeping range that a detector may pivot may be larger than the corresponding view during acquisition. In some cameras, the sweeping range that a detector may pivot may be unlimited (e.g., the detector may pivot a full 360 degrees), while in some embodiments the sweeping range of a detector may be constrained, for example over 180 degrees (from a −90 degree position to a +90 degree position relative to a position oriented toward the center of the bore).

With continued reference to FIG. 1, the depicted processing unit 120 is configured to dynamically determine, during a primary image acquisition, at least one boundary of an acquisition range corresponding to an uptake value of an object to be imaged for at least one of the detector units 115. The acquisition range is smaller than the sweep range, or maximum range of coverage, of the at least one detector unit 115. A primary image acquisition, as used herein, may be understood as a scanning procedure or process used to collect imaging information for reconstruction of an image.

The primary image acquisition may, for example, be performed over a specified time period or to collect a specified number of counts corresponding to an amount of information sufficient to provide a diagnostically useful resolution. For the purposes of clarity and avoidance of doubt, a scout scan, or other "pre-scan" utilized for the purposes of locating an organ or portion thereof and/or the boundaries of the patient, and/or for positioning imaging equipment but not used or not sufficient for reconstruction of an image used for diagnostic purposes, are not examples of a primary image acquisition. The processing unit 120 is also configured to control the at least one detector unit 115 to acquire imaging information over the acquisition range.

Figure 3:
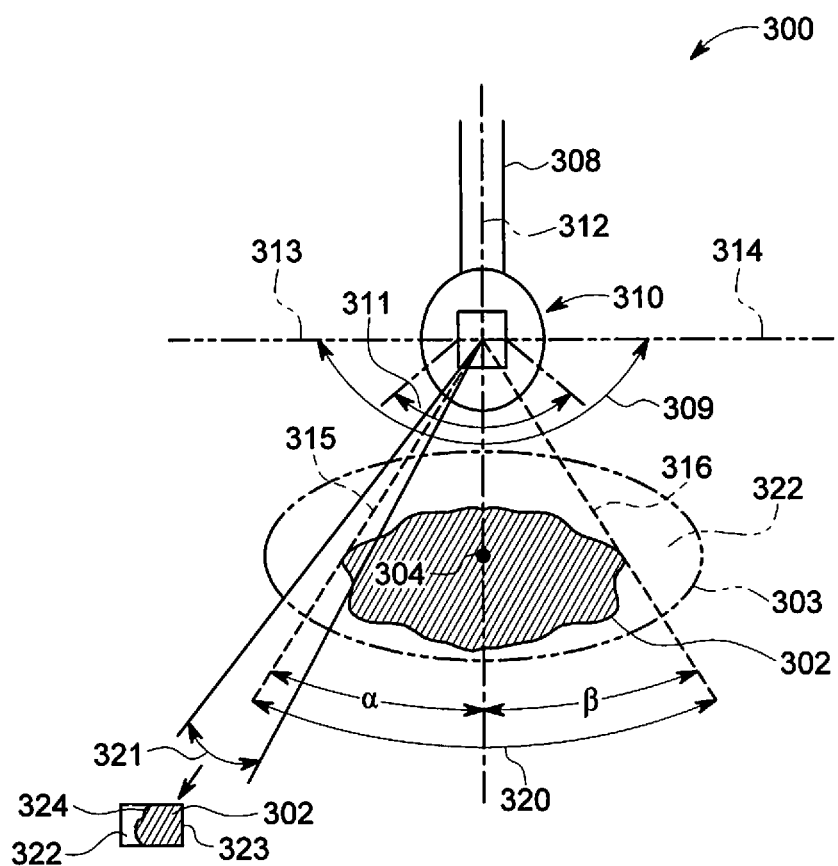
FIG. 3 depicts sweep and acquisition ranges for a detector unit according to an embodiment.

FIG. 3 depicts sweep and acquisition ranges for a detector unit 300 according to various embodiments. As seen in FIG. 3, the detector unit 300 includes a detector head 310 disposed at an end of a detector arm 308. In FIG. 3, only one detector unit 300 is depicted for ease and clarity of illustration. It may be noted that the detector unit 300 may be part of an arrangement of plural detector heads, such as depicted in FIGS. 1 and 2, and that the general principles discussed in connection with the detector unit 300 may be applied to one or more additional detector units of a multi-head camera imaging system. In FIG. 3, the detector unit 300 may be used to acquire imaging information (e.g., photon counts) of an object 303 having a region of interest 302. In the illustrated embodiment, the region of interest 302 (or ROI 302) is surrounded by surrounding tissue 322. The region of interest 302, for example, may be an organ such as the heart or brain (or portion thereof), and may have a substantially larger uptake of an administered radiopharmaceutical than surrounding tissue 322 of the object 303. A central axis 312 of the detector unit 300 passes through a center 304 of the region of interest 302 (which is disposed at the center of a bore in the illustrated embodiment). The central axis 312, for example, may correspond to a line along the view corresponding to the detector unit 300 when the detector unit 300 is at a midpoint of a range of coverage of the detector unit 300, and/or may be aligned with a central axis of the detector arm 308 to which the detector head 310 is attached.

In the illustrated embodiment, the detector unit 300 is depicted as aligned with the central axis 312, and may be rotated, pivoted or swept over a sweep range 309 between a first limit 313 and a second limit 314. In the illustrated embodiment, the first limit 313 and the second limit 314 define a sweep range 309 (or maximum range of coverage) of 180 degrees. In other embodiments, the sweep range 309 and/or relative positions of the first limit 313 and second limit 314 may vary from the depicted arrangement. It may be noted that the sweep range 309 provides more coverage than is required to collect imaging information of the region of interest 302. Thus, if the detector unit 300 is swept over the sweep range 309 during a duration of an imaging acquisition, information that may be not be useful for diagnostic purposes (e.g., information towards the ends of the sweep range 309 that does not include information from the region of interest 302) may be collected. The time used to collect the information that is not useful for diagnostic purposes may be more efficiently spent collecting additional information from the region of interest 302. Accordingly, in the illustrated embodiment, the detector unit 310 may be controlled (e.g., by processing unit 120) to be swept or pivoted over an acquisition range 320 instead of over the entire sweep range 309 during acquisition of imaging information.

As seen in FIG. 3, the acquisition range 320 generally corresponds to edges of the region of interest 302, and is bounded by a first boundary 315 and a second boundary 316. The first boundary 315 is located at an angle α in clockwise direction from the central axis 312 (and, in the illustrated embodiment, from the center 304). The second boundary 316 is located at an angle β in a counterclockwise direction from the central axis 312 (and, in the illustrated embodiment, from the center 304). The locations of the first boundary 315 and the second boundary 316 may be determined, for example, using uptake information acquired as the detector 300 sweeps over at least a portion of the sweep range 309. For example, when a photon count exceeds a predetermined threshold (or predetermined rate of change), a boundary of the region of interest 302 (for which the uptake is higher than surrounding tissue) may be determined or identified. If the photon count is increasing past a threshold, a beginning boundary of the region of interest 302 may be determined, and if the photon count is decreasing past a threshold, an ending boundary of the region of interest 302 may be determined.

It may be noted the boundaries may not necessarily correspond to a central axis or portion of a field of view of the detector unit, but may correspond to an edge or other portion of the field of view. Further, the acquisition range 320 may be configured in various embodiments to include surrounding tissue beyond the region of interest 304 (e.g., to provide background information and/or a margin of error), and/or to omit a portion of the region of interest (e.g., to focus acquisition time even more strongly on a central portion of the region of interest that may be of particular or emphasized interest). For example, the acquisition range 320 may include an amount of background or surrounding tissue for a first phase of an acquisition period and omit background or surrounding tissue for a second phase.

Figure 4:
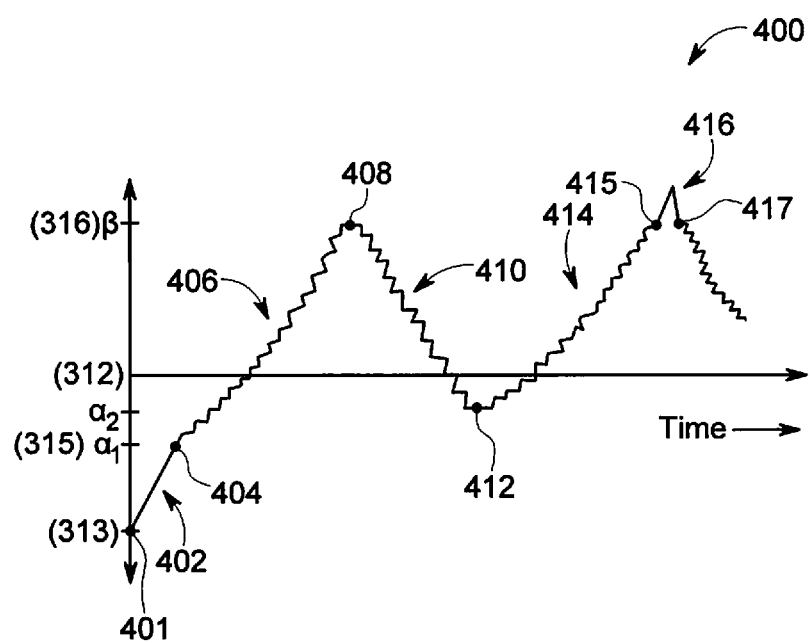
FIG. 4 illustrates an example scenario of control of the sweep of a detector unit in accordance with an embodiment.

FIG. 4 illustrates an example scenario 400 of control of the detector unit 300 during a primary image acquisition period. The detector unit 300 begins the example scenario at an initial position 401. In the illustrated embodiment the initial position 401 corresponds to the first limit 313. In some embodiments, the initial position may be located between the first limit 313 and the first boundary 315 of the acquisition range 320. For example, the initial positon 401 may be estimated based on a patient size and/or type of scan to be performed, with the initial position 410 selected to be located a distance outside of an expected acquisition range. During an initial portion 402, the detector unit 300 is swept in a counterclockwise direction from the first limit 313 and toward the central axis 312. As the detector unit 300 is swept, photon counts acquired by the detector unit 300 may be sampled and analyzed. When the photon counts reach a predetermined threshold (or a rate of increase of photon counts reaches a predetermined threshold), or the photon counts otherwise satisfy a metric configured to identify an increase in counts corresponding to the region of interest 302 (or portion thereof) entering a field of view of the detector unit, a first boundary of an acquisition range (e.g., acquisition range 320) may be determined at point 404. At point 404, the detector unit 300 may be controlled to acquire imaging information of the region of interest 302. For example, the detector unit 300 may be swept at a first speed over the initial portion 402 starting from the initial position 401. However, at 404, where the first boundary of the acquisition range begins, the detector unit 300 may be swept at a second speed that is slower than the first speed. Accordingly, relatively less time is spent covering the initial portion 402 and relatively more time is spent collecting imaging information for the region of interest over the acquisition range. In the illustrated embodiment, the point 404 corresponding to the first boundary 315 is depicted as occurring at an angle α1, which may have the same value as α of FIG. 3.

Next, during portion 406, the detector unit 300 is swept counterclockwise at an acquisition speed until the second boundary 316 of the acquisition range 320 is reached. The second boundary 316 may be determined, for example, based on a decrease in the photon count satisfying a metric (e.g., threshold) corresponding to the transition from the region of interest 302 (which has a relatively high uptake and relatively high photon count) to a surrounding portion of the object 303 (which has a relatively low uptake and relatively low photon count). It may be noted that the particular metrics or thresholds used to identify the boundaries of the acquisition range 320 may be designed or selected to provide a margin of error such that the acquisition range 320 covers an amount of surrounding tissue in addition to the region of interest 302. At 408, with the second boundary 316 identified and reached, the detector unit 300 may be reversed in direction and controlled to start rotating clockwise toward the first boundary 315. Thus, the detector unit may be controlled to reverse direction responsive to a reduction in acquired photon counts.

In some embodiments, the detector unit 300 may be controlled to rotate until the already determined first boundary is met, at which point the detector unit 300 may be again reversed to rotate counterclockwise. In the illustrated embodiment, the detector unit 300 may be controlled to update at least one of the first boundary 315 or the second boundary 316 during an acquisition period. In some embodiments, for example, the first and/or second boundaries may be updated during each cycle of an acquisition period. In some embodiments, for example, the first and/or second boundaries may be updated at predetermined intervals (e.g., every 30 seconds, every minute, every other cycle, or every fifth cycle, among others). In the illustrated embodiment, during portion 410 of the example scenario, the photon counts may be collected and analyzed as the detector unit 300 rotates or sweeps toward the first boundary 315. In the illustrated embodiment, a metric corresponding to a decrease in photon count associated with a boundary of the region of interest 302 is encountered at point 412, or with the detector unit 300 rotated at an angle α2 from the central axis 312. As seen in FIG. 4, α2 differs from α1, and the first boundary accordingly may be updated to reflect a change in the uptake of the region of interest 302 over time, and/or a change in position of the region of interest 302. Accordingly, during an imaging acquisition, one or more boundaries may be updated to further focus time spent during an acquisition on portions of an object for which an increased level of uptake is present for improved image quality, while reducing time spent on portions of the object that are not of interest.

In the illustrated embodiment, the detector head reverses direction at 412 and rotates during portion 414 until the second boundary is reached (or updated) at 415. As seen in FIG. 4, after point 415, the detector head is rotated past the second boundary and then back toward the second boundary (e.g., at a faster speed than used during portion 414). The acquisition during portion 416 may be understood as occurring for a supplemental acquisition zone, and may be utilized to collect background information and/or provide a margin of error or buffer zone at the end of the acquisition range. While one supplemental acquisition zone for the second boundary is shown in the illustrated embodiment, it may be noted that a supplemental acquisition zone may be utilized in connection with the first boundary as well. Supplemental acquisition zones in various embodiments may be utilized, for example, during each back and forth sweeping cycle of a detector head, or as another example, at predetermined intervals (e.g., every 30 seconds, every minute, every other cycle, or every fifth cycle, among others). At point 417, the second boundary is again reached and the detector is swept toward the first boundary at an acquisition speed. The acquisition speed is depicted in the illustrated embodiment as occurring as a number of steps of predetermined duration. The detector head may be swept back and forth between the first and second boundaries during all or a portion of an acquisition period. For example, in some embodiments, the detector head may be swept over the sweep range or maximum range (or other range larger than the acquisition range) to collect background information over a portion of an acquisition period.

It may be noted that the control of the sweep of the detector unit 300 may be performed using only imaging information from the particular view corresponding to the detector unit 300, and using only imaging information collected by the particular detector unit 300. Information from other views or other detectors may not be utilized in various embodiments, and the use of pre-scans or associated calculations may be eliminated or reduced. It may be noted that each detector unit may have a dedicated processor (e.g., located on-board the detector unit) that performs all or a portion of the calculations required to determine the first and second boundaries for that particular detector unit.

As indicated herein, two or more of the detector units (e.g., 310(a), 310(b), 310(c) . . . ) may each be controlled using imaging information acquired by the particular detector unit (e.g., using a control scheme utilizing one or more aspects of example scenario 400). Thus, in various embodiments, the processing unit 120 (which may include individual processors disposed on-board the detectors) may independently determine corresponding acquisition ranges for at least two of the detector units 210, and independently control the at least two of the detector units over the corresponding acquisition ranges. For example, in some embodiments, all of the detector units 210 may be independently controlled to acquire imaging information over a particular acquisition range unique to a given detector unit using imaging information only from that given detector unit.

In alternate embodiments, only some of the detector units may be controlled in accordance with a control scheme incorporating at least some aspects of the the example scenario 400 (e.g., determination of boundaries of an acquisition range using dynamically acquired imaging information and control of the detector unit over the determined acquisition range), while at least one additional detector unit may be controlled to acquire imaging information over a range that is larger than an acquisition range determined based on uptake values associated only with a given detector unit. As one example, detector units 210(a), 210(c), 210(e), 210(g), 220(i), 220(k) may be controlled as disclosed herein, whereas detector units 210(b), 210(d), 210(f), 210(h), 210(j), 210(l) may be controlled to collect information over an entire sweep range or other range.

For example, as seen in FIG. 3, some detector units may be controlled to acquire information over a corresponding acquisition range 320 as discussed herein, while others are controlled to acquire information over a larger range 311. Thus, for example, multiple structures of interest having different uptake rates may be analyzed, with one or more detectors collecting information for a particular region of interest (e.g., region of interest 302), and one or more other detectors collecting information for a different and/or larger region of the object 303.

In some embodiments, the larger range 311 may coincide with the sweep range 309 or maximum available range of a detector unit. In other embodiments, the larger range 311 may be predetermined based on estimates and/or measurements of the object 303 or portions thereof. In some embodiments, the larger range 311 may be determined using a control scheme incorporating one or more aspects of the example scenario 400, but using different (e.g., lower) thresholds or metrics than used to determine the acquisition range 320.

Returning to FIG. 1, the processing unit 120 is operably coupled to the detector units 115, and acquires imaging information from at least one detector head 115, and determines boundaries of an acquisition range for the at least one detector unit 115, for example, based on photon counts encountered during a sweep or pivoting of the detector unit 115.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may distributed among various units or housings (e.g., one or more aspects of the processing unit 120 may be disposed onboard one or more detector units, and one or more aspects of the processing unit 120 may be disposed in a separate physical unit or housing). The processing unit 120 may perform various operations in addition to the determination of acquisition range boundaries and control of detector heads. For example, the processing unit 120 may reconstruct an image using information acquired during primary image acquisition via the detector units 115. It may be noted that operations performed by the processing unit 120 (e.g., operations corresponding to process flows or methods discussed herein, or aspects thereof) may be sufficiently complex that the operations may not be performed by a human being within a reasonable time period. For example, analyzing photon counts to identify boundaries of an acquisition range, providing control signals to detector units, or the like may rely on or utilize computations that may not be completed by a person within a reasonable time period.

In the illustrated embodiment, the processing unit 120 includes a determination module 122, a control module 124, and a memory 130. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

In the illustrated embodiment, the depicted determination module 122 is configured to, responsive to received photon counts, identify boundaries of an acquisition range as disclosed herein. It may be noted that, in various embodiments, aspects of the determination module 122 may be distributed among detector units 115. For example, each detector unit may have a dedicated determination module disposed in the head 116 of the detector unit 115. It may be noted that in various embodiments the determination of boundaries of an acquisition range of a given detector unit is determined using imaging information only from the given detector unit, or without using imaging information from any other detector unit.

The depicted control module 124 is configured to, responsive to boundaries determined by the determination module, control one or more detector heads 116 to sweep over a corresponding acquisition range. For example, responsive to an increased photon count (e.g., a photon count satisfying a predetermined metric corresponding to reaching or approaching the beginning of a range covering a region of interest), the control module 124 may control a detector head to continue sweeping in an initial direction, but at a slower speed than an initial speed utilized before the increased photon count. As another example, responsive to a decreased photon count (e.g., a photon count satisfying a predetermined metric corresponding to reaching or approaching the end of a range covering a region of interest), the control module 124 may control a detector head to reverse direction of sweep. It may be noted that, in various embodiments, aspects of the control module 124 may be distributed among detector units 115. For example, each detector unit may have a dedicated control module disposed in the head 116 of the detector unit 115.

The memory 130 may include one or more computer readable storage media. The memory 130, for example, may store information describing previously determined boundaries of acquisition ranges, predetermined thresholds or other metrics utilized for determining boundaries of acquisition ranges, parameters to be utilized during performance of a scan (e.g., speed of rotation for acquisition range, speed of rotation for supplement zone, time or total count value over which an acquisition is to be performed), or the like. Further, the process flows and/or flowcharts discussed herein (or aspects thereof) may represent one or more sets of instructions that are stored in the memory 130 for direction of operations of the imaging system 100.

It may be noted that while the processing unit 120 is depicted schematically in FIG. 1 as separate from the detector units 115, in various embodiments, one or more aspects of the processing unit 120 may be shared with the detector units 115, associated with the detector units 115, and/or disposed onboard the detector units 115. For example, in some embodiments, at least a portion of the processing unit 120 is integrated with at least one of the detector units 115. In various embodiments, at least a portion of the processing unit 120 includes at least one application specific integrated circuit (ASIC) or field programmable gate array (FPGA) that is disposed onboard or integrated with at least one of the detector units.

Figure 5:
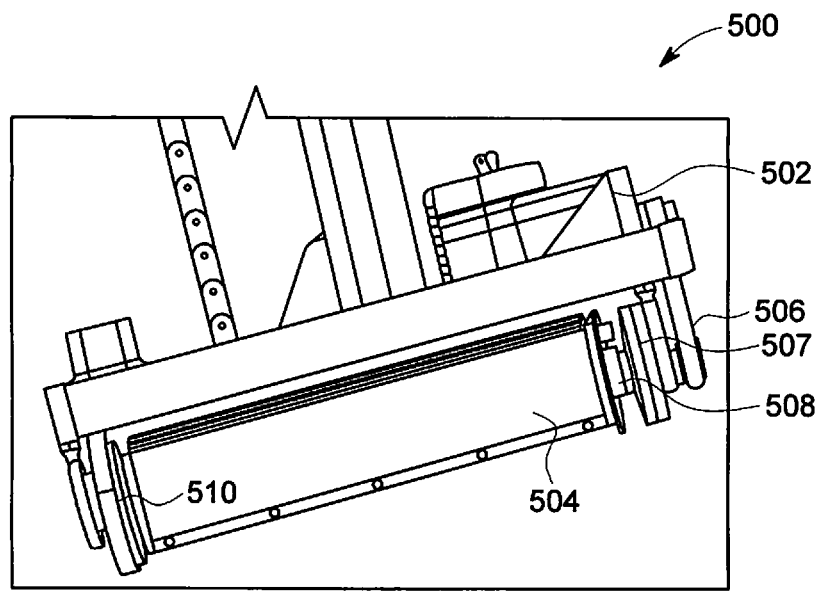
FIG. 5 provides a schematic view of a detector head in accordance with an embodiment.
Figure 6:
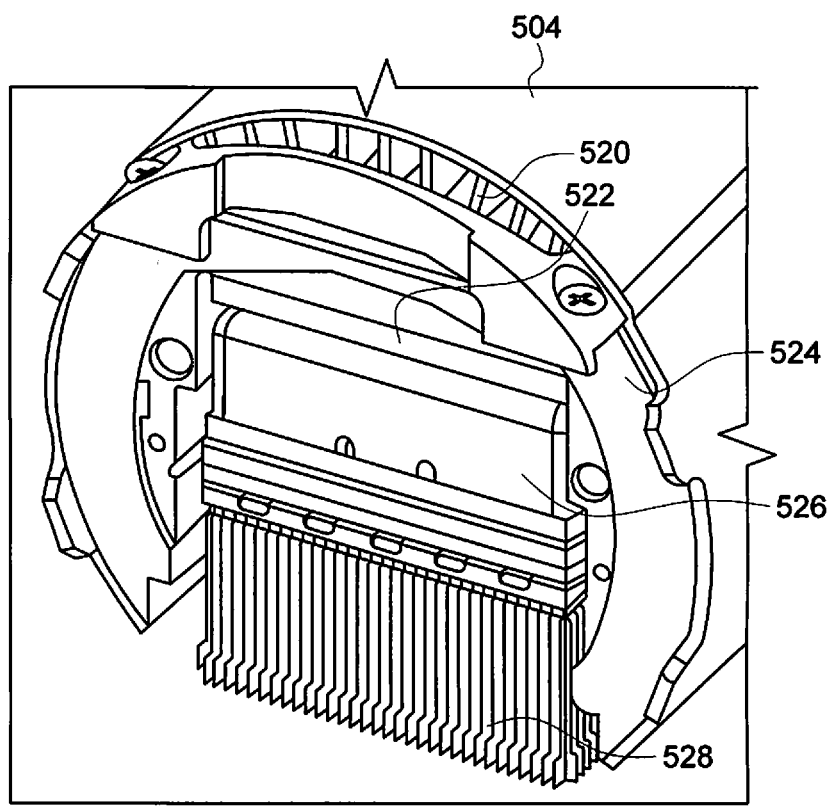
FIG. 6 shows a sectional view of the detector head of FIG. 5.

FIG. 5 is a schematic view of an example detector head 500 formed in accordance with various embodiments, and FIG. 6 is a sectional view of the detector head 500. As seen in FIG. 5, the detector head 500 includes a stepper motor 502 that may be utilized to pivot a detector column 504. It may be noted that motors other than stepper motors may be used in various embodiments. It may also be noted that the steps depicted in FIG. 4, for example, do not necessarily correspond to the elemental steps of the stepper motor 502. It may further be noted that continuous motion (e.g., of varying speeds) may be utilized in embodiments of the invention, instead of the staircase type motion depicted in FIG. 4. Generally, "step and shoot" motion may be employed in various embodiments. In step and shoot motion, the detector is rapidly pivoted, and then remains stationary during data collection. Step and shoot motion may be utilized in various embodiments to eliminate or reduce power transients and/or other electronic noise associated with activation of electrical motors. Use of step and shoot motion may also be utilized to eliminate orientation uncertainties associated with each collected photon. However, it may be noted that, in various embodiments, with fine orientation encoders, and frequent sampling of the orientation encoders, detector aiming may be associated with each detected photon to sufficient accuracy even if the detectors are continuously pivoting during data acquisition. The detector column 504, for example, may include a shield, a processing board, a detector (e.g., a CZT detector) and a collimator. The detector head 500 also includes a gear 506 coupling the stepper motor to the column 504, as well as a slip ring 507 (configured to allow for transfer of signals between the rotating detector column 504 and non-rotating components) and a multiplex board 508. In the illustrated embodiment, the detector head 500 also includes an air channel 510 configured to provide cooling to components of the detector head 500. As seen in FIG. 6, the detector column 504 includes a heat sink 520, a printed circuit board 522 (which may incorporate one or more aspects of the processing unit 120), a lead shielding 524, a CZT detector module 526, and collimator 528 that is registered to the CZT detector module 526 in the illustrated embodiment. Additional details and discussion regarding detector heads is provided in U.S. patent application Ser. No. 14/671,039, entitled "Reduced Airborne Contamination Detector Heads," filed Mar. 27, 2015, the subject matter of which is hereby incorporated by reference in its entirety.

Figure 7:
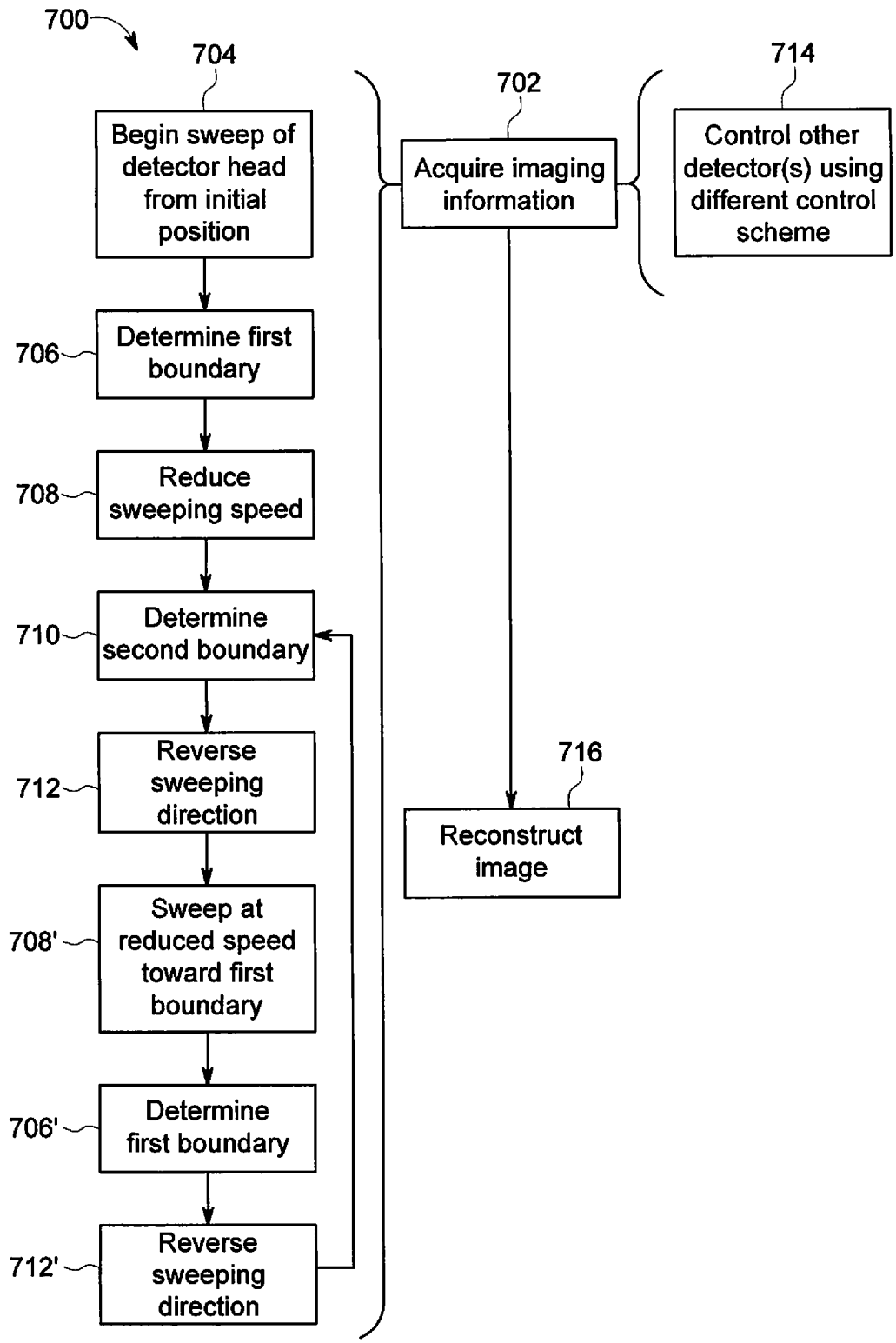
FIG. 7 shows a flowchart of a method, according to an embodiment.

FIG. 7 provides a flowchart of a method 700 for controlling detector heads of a multi-head imaging system in accordance with various embodiments. The method 700 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the processing unit 120) to perform one or more operations described herein.

At 702, imaging information is acquired. For example, in various embodiments, imaging information may be acquired as a primary imaging acquisition that will be used to reconstruct an image to be used for diagnostic purposes. The imaging information for the depicted embodiment is acquired with plural detector units mounted to a gantry defining a bore configured to accept an object to be imaged. As discussed herein, each detector unit defines a corresponding view oriented toward a center of the bore, with each detector unit configured to acquire the imaging information over a sweep range corresponding to the view of the given detector unit.

At 704, as part of the acquisition of imaging information in the illustrated embodiment, at least one of the detector units may begin a sweep from an initial point toward a region of interest. The initial point in some embodiments may be at a limit of a maximum sweep range of the detector unit. In other embodiments, the initial point may be determined based on a priori knowledge, such as a size of a patient and/or a type of scan being performed. The detector unit may be swept at a relatively high speed as it is swept from the initial point toward the region of interest.

At 706, a first boundary of an acquisition range for at least one of the detector units is determined. The acquisition range is smaller than the sweep range, thereby focusing additional acquisition time on the region of interest, improving image quality and/or reducing an overall or total acquisition time. The first boundary, for example, may correspond to a transition within the field of view of the rotating detector unit from tissue surrounding a region of interest to at least a portion of the region of interest itself being disposed within the field of view. For example, the first boundary may correspond to a position at which one-half (or other fraction) of the region of interest is within the field of view of the detector unit. As another example, the first boundary may be defined when the edge of the ROI is nearing the end of the FOV, while at least a substantial part of the FOV is viewing the ROI. In various embodiments, a substantial part of the FOV may be understood as, for example, over 50% of the area defined by the FOV, over 75% of the area defined by the FOV, or over 90% of the area defined by the FOV, as examples. For example, as seen in FIG. 3, an FOV 321 taken at the first boundary 315 corresponds to an image view 323 shown in FIG. 3. In the image view 323, an edge 324 between the ROI 302 and surrounding tissue 322 is located near an edge of the image view 323 or FOV 321. In the depicted embodiment, the first boundary is dynamically determined during the primary image acquisition. The first boundary corresponds to, and may be determined based on, an uptake value of the object to be imaged. For example, the uptake value associated with the first boundary is larger than the uptake value for tissue surrounding the region of interest. The first boundary in various embodiments is determined based on a change of photon counts acquired by the detector unit. For example, the first boundary may be determined when the photon counts acquired by the detector unit increase to a level satisfying a predetermined threshold or metric.

At 708, responsive to the determination and identification of the first boundary, the speed of the sweeping or pivoting of the detector unit is reduced from an initial speed to an acquisition speed, with the detector unit still sweeping in the same direction.

At 710, as the detector unit continues to sweep in the initial direction, a second boundary of the acquisition range is determined. The second boundary, for example, may correspond to a transition within the field of view of the rotating detector unit from the region of interest itself (or a portion thereof) being disposed within the field of view to tissue surrounding the region of interest being disposed within the field of view. For example, the second boundary may correspond to a position at which one-half (or other fraction) of the region of interest is within the field of view of the detector unit. In the depicted embodiment, the second boundary is dynamically determined during the primary image acquisition. The second boundary corresponds to, and may be determined based on, an uptake value of the object to be imaged. The second boundary in various embodiments is determined based on a change of photon counts acquired by the detector unit. For example, the second boundary may be determined when the photon counts acquired by the detector unit decrease to a level satisfying a predetermined threshold or metric.

At 712, responsive to the determination and identification of the second boundary, the direction of the sweeping or pivoting of the detector unit is reversed, with the detector unit swept toward the first boundary. This is schematically depicted in FIG. 7 by the optional steps 708' (sweeping at reduced speed toward the first boundary), 706' (determining the first boundary), and 712' (again reversing the sweeping direction until the second boundary is determined or reached at 710). It may be noted that in some embodiments, at 706', the previously determined first boundary may be utilized as a point at which the sweeping is reversed.

Figure 8:
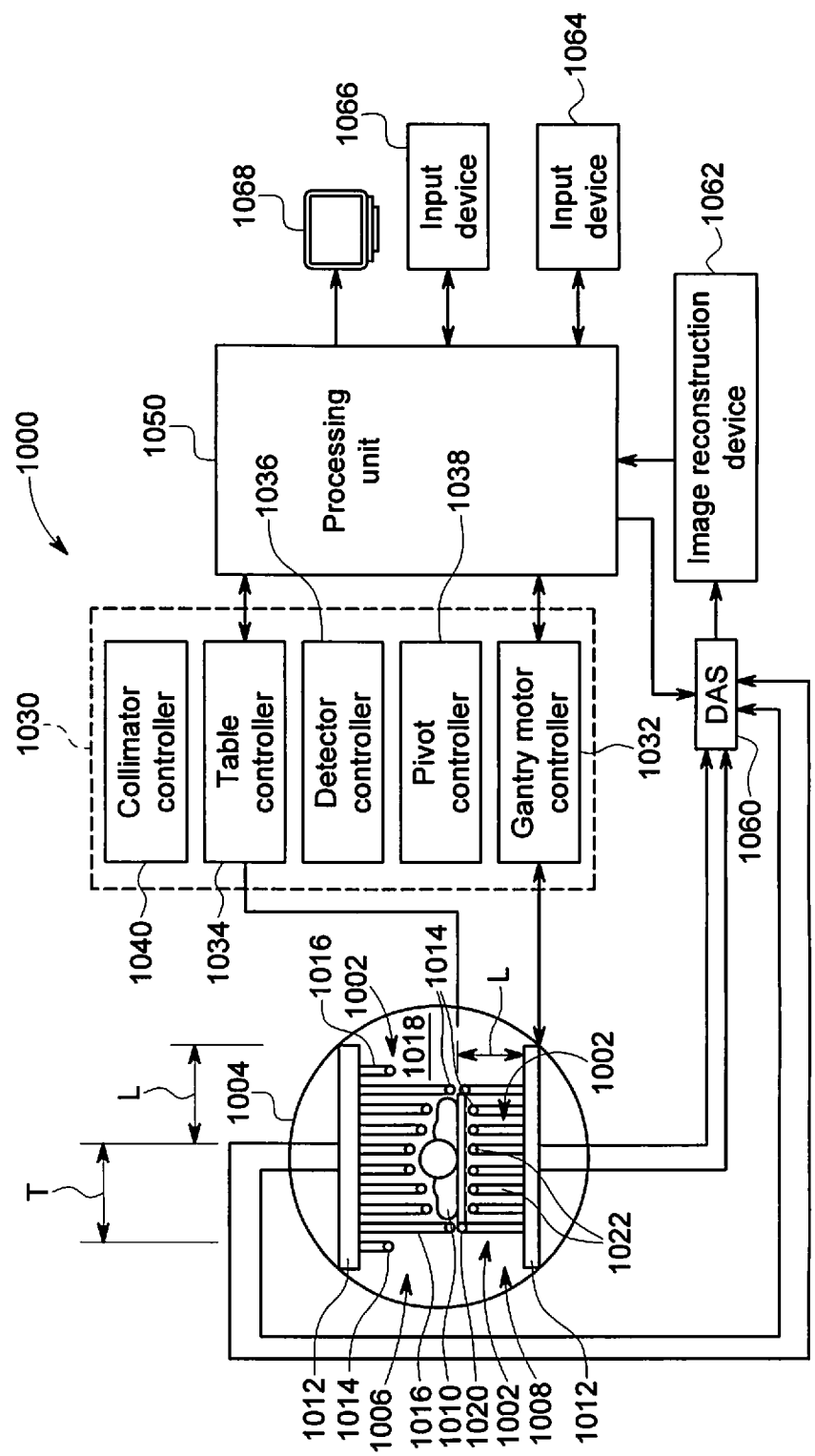
FIG. 8 shows a schematic view of an imaging system, according to an embodiment.

It may be noted that the detector unit may be swept back and forth between the first and second boundaries until an acquisition period is completed. The acquisition period may have a duration corresponding to an amount of time or a number of photon counts sufficient to provide a desired resolution or image quality. As discussed herein, the first and second boundaries may be updated during the image acquisition in various embodiments. It may further be noted that multiple detectors may be independently controlled, for example using one or more aspects of steps 704-712. Further, in some embodiments, one or more detectors may be controlled pursuant to steps 704-712, while one or more other detectors are controlled pursuant to a different control scheme, as indicated at 714. It should be noted that acquiring imaging information 702 may be concurrent to steps 704-712'. Optionally, when the pivoting and sweeping represented by the chain of steps 712' is completed (or a given number of iterations of the chain of steps is completed), a gantry (e.g., gantry 110) may rotate (or shift as gantry 1004 of FIG. 8 is configured to shift) to move the detector heads slightly, and the chain of steps 704-712' may be repeated while the detector heads are in different positions with respect to the patient. For example, the one or more other detectors may acquire imaging information over a range larger than an acquisition range corresponding to the region of interest, for example, to acquire additional background information and/or to acquire information of a different or additional region of interest. The one or more other detectors may be configured to acquire imaging information corresponding to one or more additional regions of interest that corresponds to uptake of a different radiopharmaceutical than the region of interest corresponding to the acquisition range of steps 704-712.

At 716, when the primary acquisition duration has been satisfied, an image is reconstructed using imaging information acquired during the primary acquisition. It may be noted that the imaging information used to dynamically adjust the sweeping of at least some of the detector units is also used to reconstruct the image.

In some embodiments, a detector head (or detector heads) may start the imaging data acquisition with an FOV of one or more heads pointing directly to the center of the bore, or to another position at which the FOV is entirely viewing the ROI. When aimed at the center of the bore, the ROI is within the FOV, and it is most likely that the narrow FOV is entirely viewing the ROI. The detector head (or heads) may then pivot at reduced speed until the second boundary is encountered and determined. The method may then continue as discussed herein, following steps 712, 708', 706' 712', 710 and so on. Alternatively, a detector head (or heads) may begin being pointed at the center of the bore or other position at which the FOV is entirely viewing the ROI, and rotate or pivot toward the first boundary.

In some embodiments, it may be beneficial to reconstruct the entire object 303, with the ROI 302 reconstructed at an enhanced resolution and/or at an enhanced accuracy. Accordingly, more dwell time may be spent while the FOV is aimed at the ROI, and less dwell time while the FOV is aimed at parts of the object 303 (e.g., surrounding tissue 322) which are outside of the ROI 302. Accordingly, in some embodiments, two additional boundaries may be determined: first and second object boundaries at the two ends of the larger range 311 or other range that includes portions of the surrounding tissue 322. Sweeping of a detector head may then proceed at a fast or intermediate rate between first object boundary and first boundary (e.g., while viewing the surrounding tissue 322), with sweeping of the detector head proceeding at a reduced rate between the first and second boundaries (e.g., while viewing the ROI 302), and again at a fast or intermediate rate between the second object boundary and the second boundary (e.g., while viewing the surrounding tissue 322).

In various embodiments, pivoting speed may remain slow, however, for N sweeps between the first and second boundaries, while there are M sweeps between the first object boundary and second object boundary. Thus, while the range between the first and second boundaries corresponding to the ROI is swept N+M times, the range outside the ROI is swept only M times.

Similarly, the sweeping sequence, in some embodiments may be: from the first object boundary to the second boundary, then reverse direction and sweep to the first boundary, then reverse direction and sweep to the second object boundary, and then reverse the sequence. In this way, the ROI is sampled twice as long as the non-ROI parts of the object.

It may be noted that, usually, the radioisotope concentration in the non-ROI parts of the object is reduced compared to the radioisotope concentration in the ROI parts of the object. However, this may not always be the case, as voids or parts of the body having less affinity, and/or defects in parts of body, may be the subject of the imaging, and thus included in the ROI. It may be noted that the radioisotope concentration in the non-ROI parts of the object may generally be high enough to distinguish the non-ROI parts of the object from regions outside the object where no radiation is emitted at all. Thus, the determination of the object boundaries is generally possible (e.g., by utilizing a lower threshold for determination of the first and second object boundaries compared to the first and second boundaries corresponding to the ROI).

Embodiments described herein may be implemented in medical imaging systems, such as, for example, SPECT, SPECT-CT, PET and PET-CT. Various methods and/or systems (and/or aspects thereof) described herein may be implemented using a medical imaging system. For example, FIG. 8 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 8 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 8. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 8). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004.

In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 8 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 8 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

Figure 9:
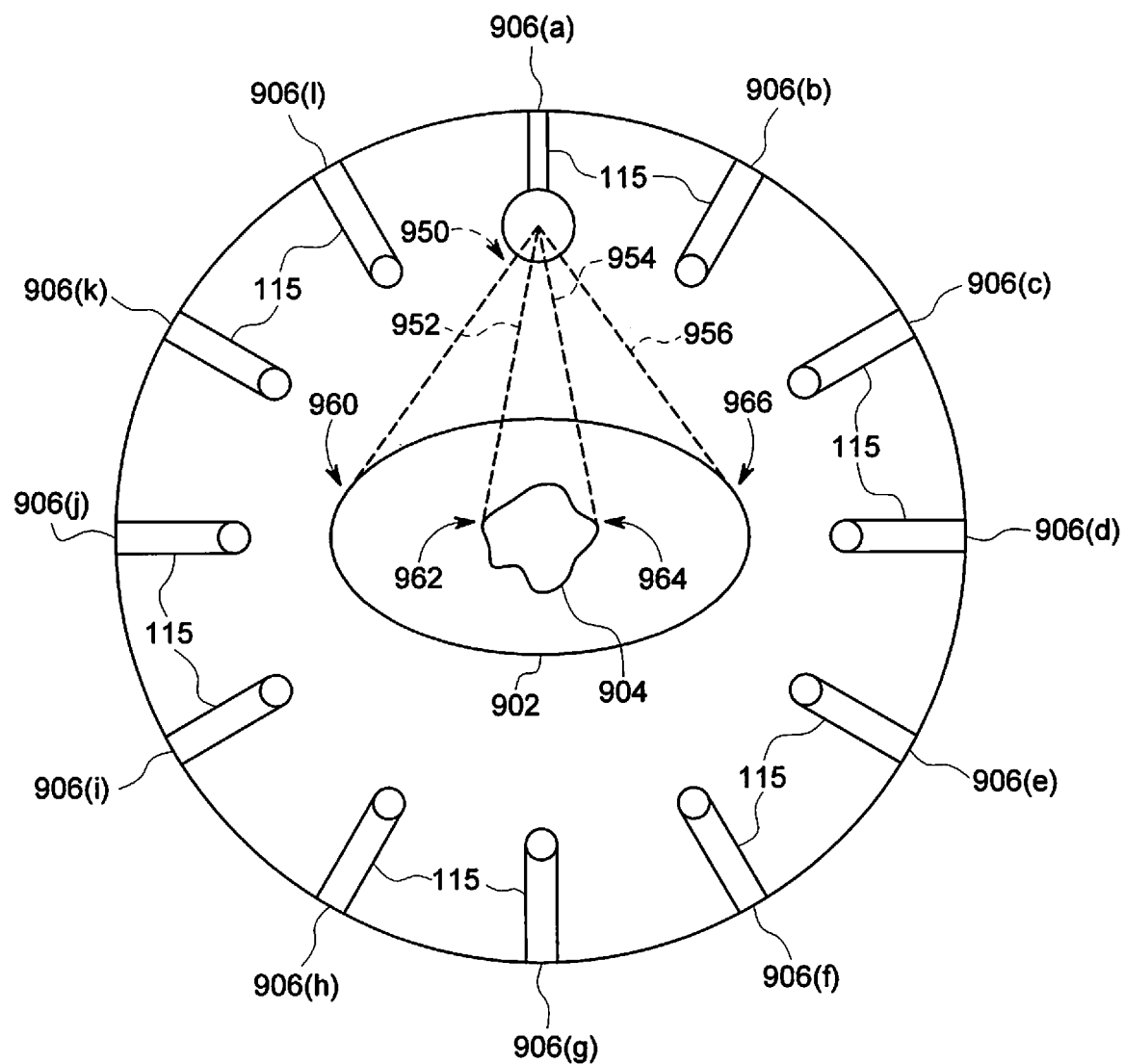
FIG. 9 depicts detector unit positions in accordance with various embodiments.

In various embodiments, scan parameters may be determined, for example, using imaging information (e.g., photon counts) acquired at the beginning of a scan without reconstructing any images. For example, with continued reference to FIG. 1, each detector unit 115 may also be understood as defining a detector unit position. For example, FIG. 9 depicts an example imaging system 900 including detector units 115 disposed at 12 positions (906(*a*)-906(*l*)) around an object 902 to be imaged. It may be noted that the detector units 115 may be configured generally similarly in various respects to the detector units 115 discussed in connection with FIG. 1. For example, each detector unit 115 may include an arm 114 and a head 116 as shown in FIG. 1. The object 902 includes a volume of interest 904. For example, the object 902 may be a human patient and the volume of interest 904 may be one or more organs of the patient that are to be evaluated using a scan performed with the imaging system 900.

The processing unit 120 in various embodiments is configured to determine plural angular positions (e.g., positions along a sweep range) for each detector unit 115, with the angular positions corresponding to boundaries of the object 902 to be imaged. As seen in FIG. 9, a first angular position 950 (defining a viewing angle of a detector unit) corresponds to a first boundary 960 between air and soft tissue, a second angular position 952 corresponds to a first boundary 962 between soft tissue and the volume of interest 904, a third angular position 954 corresponds to a second boundary 964 between the volume of interest 904 and soft tissue, and a fourth angular position 956 corresponds to a second boundary 966 between soft tissue and air. Angular positions for only the first detector unit position 906(*a*) are shown in FIG. 9 for purposes of clarity and ease of illustration; however, it may be noted that corresponding angular positions and boundaries may be employed for the remaining detector unit positions 906(*b*)-(*l*). The boundaries between air and tissue, or between different types of tissue, may be determined for example, based on photon counts acquired during one or more preliminary sweeps of the detector unit 115 across the object 902. For example, a first amount of increase (or decrease) in photon counts may be used to determine a transition between air and soft tissue outside of the volume of interest, while a second amount of increase (or decrease) in photon counts may be used to determine a transition between the volume of interest and soft tissue outside of the volume of interest. It may be noted that other detector arrangements may be employed in alternate embodiments. For example, the views used to construct a representation such as a plot and generate curves or another model used to determine scan parameters may be views that are arranged along a length of a patient (e.g., a series of views or slabs used to image a volume of interest such as the spinal cord).

Figure 10:
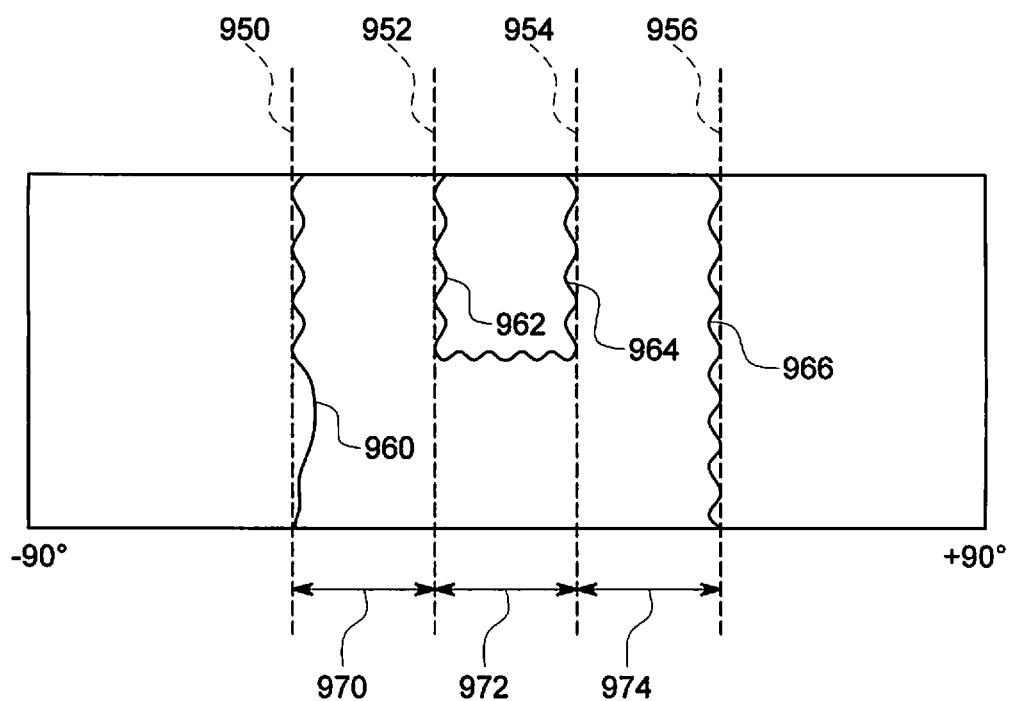
FIG. 10 depicts an example detector unit sweep range in accordance with various embodiments.

FIG. 10 provides a schematic depiction of the sweep range (e.g., projection data acquired over the sweep range) for the first detector position 906(*a*). In the depicted example, the detector unit 115 positioned at the first detector position 906(*a*) has a sweep range of −90 degrees to +90 degrees. It may be noted that, while the various angular positions are shown positioned at the various boundaries, in some embodiments the angular positions may be varied to correspond but not necessarily align with the boundaries, for example the second angular position 952 and the third angular position 954 may be selected to provide a slight offset from a corresponding boundary into the soft tissue to provide a safety margin to help ensure that the entire volume of interest 904 is imaged appropriately.

As seen in FIG. 10, three sweep range portions are defined with respect to the boundaries and angular positions within the object 902 to be imaged. In the illustrated example, a first sweep range portion 970 is defined between the first angular position 950 and the second angular position 952, a second sweep range portion 972 is defined between the second angular position 952 and the third angular position 954, and a third sweep range portion 974 is defined between the third angular position 954 and the fourth angular position 956. The first sweep range portion 970 and the third sweep range portion correspond to soft tissue of the object 902, and the second sweep range portion corresponds to the volume of interest 904. For efficient scanning, a relatively larger amount of information may be acquired for the volume of interest 904 than for soft tissue outside of the volume of interest. Accordingly, the detector unit 115 at the first detector unit position 906(*a*) may be swept at a relatively higher rate over the first sweep range portion 970 (between the first angular position 950 and the second angular position 952) and also at the relatively higher rate over the third sweep range position 974 (between the third angular position 954 and the fourth angular position 956). However, to acquire more information over the volume of interest 904 relative to soft tissue outside of the volume of interest 904, the detector unit 115 of the depicted example may be swept at a relatively lower rate over the second sweep range portion 972 (from the second angular position 952 to the third angular position 954). Each detector unit 115 of the imaging system 900 may controlled using the same general principles discussed above in connection with the first detector unit position 906(*a*). Accordingly, in various embodiments, one or more processors (e.g., processing unit 120) may be configured to sweep each detector unit 115 at a first faster rate between the first angular position 950 and the second angular position 952, sweep each detector unit 115 at a second, slower rate between the second angular position 952 and the third angular position 954, and sweep each detector unit 115 at the first rate between the third angular position 954 and the fourth angular position 956.

With continued reference to FIG. 1 along with FIGS. 9 and 10, as mentioned above, the processing unit 120 in various embodiments is configured to determine plural angular positions (e.g., first angular position 950, second angular position 952, third angular position 954, fourth angular position 956) for each detector unit 115, with the angular positions corresponding to boundaries (e.g., first boundary 960 between air and soft tissue, first boundary 962 between soft tissue of the object 902 and the volume of interest 904, second boundary 964 between the volume of interest 904 and soft tissue, and fourth boundary 964 between soft tissue of the object 902 and air) of the object 902 to be imaged.

Figure 11:
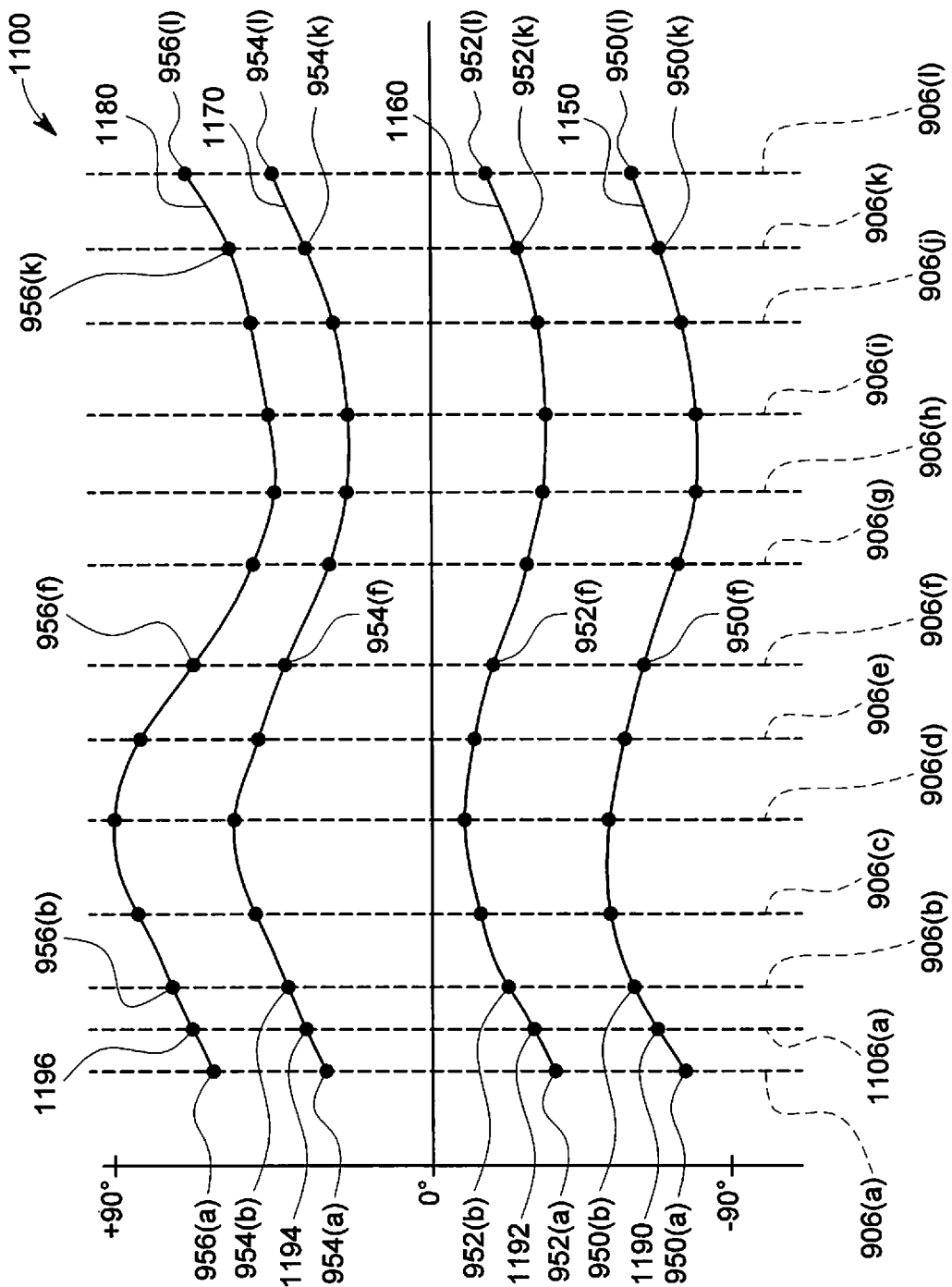
FIG. 11 depicts example angular position curves in accordance with various embodiments.

Further, the processing unit 120 may be configured (e.g., programmed) to generate a representation (e.g., plot) for each angular position for each detector unit position, and to generate a model based on the angular positions using the representation (e.g., generate an angular positional curve for each angular position using the plot or other representation). It may be noted that the plot or representation in various embodiments need not necessarily be printed or otherwise provided in a physical format, but may instead be a digital representation. Further it may be noted that, while a plot utilizing angular positional curves is discussed herein in connection with certain embodiments, other representations and models other than curves (e.g., straight and/or discontinuous lines or line segments between estimated or determined points of a plot or other representation; one or more tables including points corresponding to those discussed in connection with various embodiments discussed herein) may be utilized in various embodiments. FIG. 11 illustrates an example plot 1100 used to generate angular positional curves. In the plot 1100, detector unit position is plotted along the x-axis or horizontal axis, and angular position is plotted along the y-axis or vertical axis. The plot 1100 corresponds to the examples depicted in FIGS. 9 and 10. Accordingly, the detector unit positions are plotted from 906(*a*) to 906(*l*), and the angular positions are plotted between a range of −90 to +90 degrees. Points for each detector unit position are plotted for the four angular positions (950, 952, 954, 956) corresponding to the boundaries determined for each particular detector unit position (point 950(*a*) for the first angular position 950 for the first detector unit position 906(*a*), point 950(*b*) for the first angular position 950 for the second detector unit position 906(*b*), and so on). To generate a first angular position curve 1150, the points 950(*a*)-(*l*) corresponding to the first angular position 950 for the various detector unit positions are used. For example, the first angular position curve 1150 may be generated by determining a curve that smoothly connects the points 950(*a*)-(*l*). It may be noted that curve smoothing may be employed to determine an accurate shape as well as to correct for any points that may be anomalies or otherwise inaccurate or inconsistent. Similarly, to generate a second angular position curve 1160, the points 952(*a*)-(*l*) corresponding to the second angular position 952 for the various detector unit positions are used. For example, the second angular position curve 1160 may be generated by determining a curve that smoothly connects the points 952(*a*)-(*l*). Also, to generate a third angular position curve 1170, the points 954(*a*)-(*l*) corresponding to the third angular position 954 for the various detector unit positions are used. For example, the third angular position curve 1170 may be generated by determining a curve that smoothly connects the points 954(*a*)-(*l*). To generate a fourth angular position curve 1180, the points 956(*a*)-(*l*) corresponding to the fourth angular position 956 for the various detector unit positions are used. For example, the fourth angular position curve 1180 may be generated by determining a curve that smoothly connects the points 956(*a*)-(*l*). It may be noted that other angular positions/boundaries may be employed in other embodiments. For example, in embodiments which feature separate volumes of interest (e.g., imaging two kidneys), an additional range of soft tissue between the volumes of interest may be provided using angular positions and boundaries corresponding to transitions between soft tissue and volumes of interest. As another example, in embodiments which will pass over separate regions of air (e.g., a scan including arms in a separate position from the body), additional angular positions and boundaries may be used for additional transitions between soft tissue and air.

The processing unit 120 may also be configured to determine scan parameters to be used to image the object 902 using the angular positional curves. For example, default or initial scan parameters may be used to acquire imaging information in one or more preliminary sweeps of the object 902. The imaging information acquired during the one or more preliminary sweeps may be used to determine the angular positions and angular position curves as discussed herein. The angular position curves may then be used to determine scanning parameters for the remainder of the scanning process. Further, the angular positions and angular position curves may be updated during a scanning process and used to update the scanning parameters. The scanning parameters determined using the angular positional curves are generally settings used to acquire imaging information. As one example, a sweep range may be determined. In the depicted embodiment, the sweep range may be defined from the first angular position 950 to the fourth angular position 954. For instance, whenever a particular detector unit 115 reaches its corresponding first angular position 950 or fourth angular position 954, the detector unit 115 may reverse direction to sweep back toward the volume of interest 904. As another example, sweep rates (or speeds of rotation of a detector head as it sweeps) may be determined. In the depicted embodiment, for example, each particular detector unit 115 may be controlled to have a faster sweep rate when it sweeps between its corresponding first angular position 950 and second angular position 952, and when it sweep between its corresponding third angular position 954 and fourth angular position 956. Each particular detector unit 115 may be controlled to have a slower sweep rate when it sweeps between its corresponding second angular position 952 and third angular position 954. Other scan parameters that may be determined additionally or alternatively include the number of detector units to be employed, radial position (e.g., how close to or far from center of bore of gantry) of one or more detector units, gantry rotational position, or sequence of positioning of heads.

The positional curves may be used to determine scan parameters for a variety of benefits and/or using a variety of techniques. For example, if the angular positions determined using photon counts of a given detector at a particular detector position provides plot points that are at a distance from the angular positional curves, revised angular positions for the particular detector at the particular detector position may be determined to more closely match or align with the positional curves. Additionally or alternatively, photon counts may be acquired using less than all of the detector units disposed around a bore, with a curve generated from information collected by the detector units that were used to collect photon counts utilized to estimate or determine angular positions for other detector units that were not used. Additionally, or alternatively, in various embodiments, the processing unit 120 may determine scan parameters for at least one additional detector unit position (e.g., a detector unit position for which photon counts have not been acquired) corresponding to a rotation of the gantry. For example, the gantry 110 with the detector units 115 attached may be positioned at a first rotational position at which photon counts are acquired and used to general angular positional curves as discussed herein. Then, the gantry 110 may be rotated to a new position. The angular positional curves may be used, for example, to estimate angular positions for one or more detectors at the new rotational position of the gantry, and the angular positions at the new rotational position may be used to determine corresponding sweep ranges and/or speeds for the detectors when the imaging system 900 is used to acquire imaging information at the new rotational position.

For instance, in one example scenario, an additional detector unit position that is interposed between a first unit position of a first detector unit and a second detector unit position of a second detector unit, with the processing unit 120 configured to determine an angular position for the additional detector unit position. For example, with reference to FIG. 11, a rotation of the gantry may cause the detector unit 115 associated with the first detector unit position 906(*a*) to shift to a new position 1106(*a*) that is interposed between first detector unit position 906(*a*) and second detector unit position 906(*b*) of the previous gantry rotational position. Using the generated angular positional curves, points 1190, 1192, 1194, and 1196 may be estimated or determined to provide the angular positions for the new position 1106(*a*), which may in turn be used to determine one or more scanning parameters to be used for a detector in the new position 1106(*a*) (e.g., sweep range and/or sweep rate).

Figure 12A:
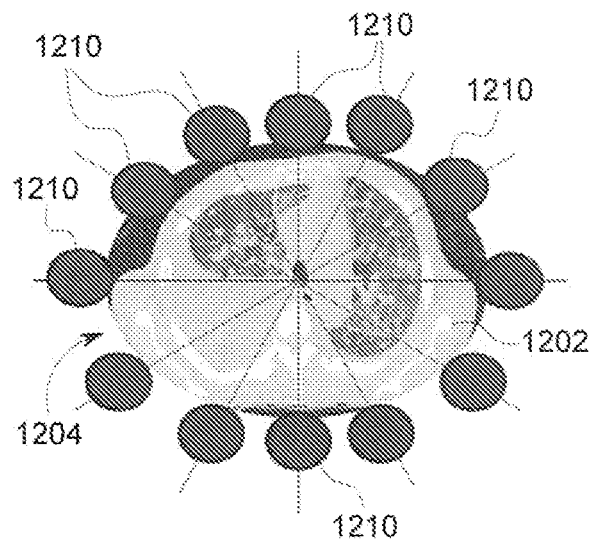
FIG. 12a depicts an example irregularly shaped footprint resulting from an irregularly shaped object.
Figure 12B:
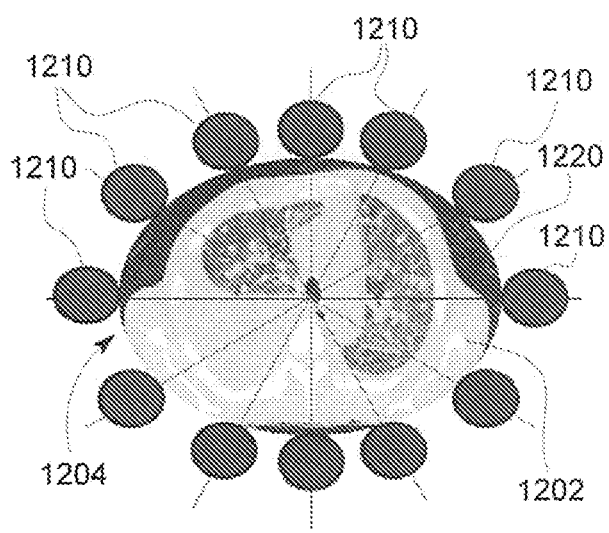
FIG. 12b depicts a regularly shaped footprint in accordance with various embodiments.

In various embodiments, the processing unit 120 may also determine one or more radial positions for detector heads to be used during scanning. For example, in various embodiments, the processing unit 120 is configured to determine a regularly shaped footprint that surrounds an irregular shape of the object 904 to be imaged, to advance at least some of the detector units 115 to the regularly shaped footprint, and to acquire imaging information with the at least some of the detector units 115 positioned at the regularly shaped footprint (e.g., with a detector head positioned at or near the regularly shaped footprint). FIG. 12*a* depicts an example irregularly shaped footprint resulting from an irregularly shaped object, and FIG. 12*b* depicts a regularly shaped footprint in accordance with various embodiments.

As seen in FIG. 12*a*, an object 1202 to be imaged has an irregular shape 1204. For example, the object 1202 has various portions that switch between convex and concave, as well as portions with rapid or discontinuous changes in curvature. In FIG. 12*a*, detector units 1210 are brought into close proximity with the object 1202; however, the positioning of the detector units 1210 in close proximity with the irregularly shaped object can affect the available sweep ranges of the detector units 1210 and/or result in imaging artifacts (e.g., due to missing information from an unavailable portion of a sweep range). For example, an unavailable portion of a sweep range may result from a limit (e.g., −90 to +90 degrees of rotation) of the sweep range, and/or due to an obstruction of part of the object by an adjacent detector. In various embodiments, to eliminate or reduce such artifacts, the detector units 1210, instead of being brought into close proximity, are advanced to a regularly shaped footprint that surrounds the irregular shape 1204. As seen in FIG. 12*b*, the detector units 1210 are advanced to a regularly shaped footprint 1220 that surrounds the irregular shape 1204 of the object 1202. In some embodiments, the irregular shape 1204 and regularly shaped footprint 1220 may share a common border at one or more portions along the perimeter of the regularly shaped footprint 1220, while in other embodiments a gap may be present along the entire perimeter between the irregular shape 1204 and the regularly shaped footprint 1220. A footprint may be understood as being regularly shaped because one or more of: the footprint is defined by a single mathematical relationship of function, the footprint is smooth and continuous, the footprint is devoid of switches between convex and concave shapes, or the footprint is devoid of rapid or discontinuous changes in curvature. In the illustrated embodiments, the regularly shaped footprint 1220 is an ellipsoid (e.g., a non-circular ellipsoid).

Figure 13:
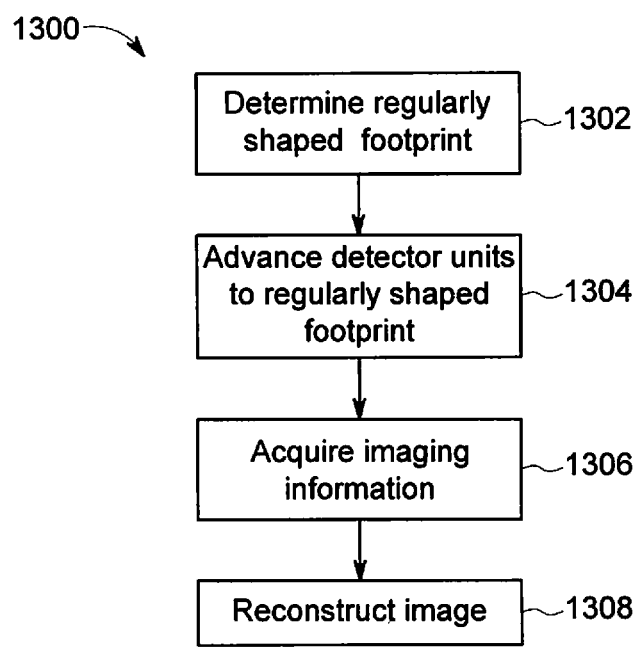
FIG. 13 shows a flowchart of a method, according to an embodiment.

FIG. 13 provides a flowchart of a method 1300 for controlling detector heads of a multi-head imaging system in accordance with various embodiments. The method 1300 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1300 may be able to be used as one or more algorithms to direct hardware (e.g., one or more aspects of the processing unit 120) to perform one or more operations described herein.

At 1302, a regularly shaped footprint is determined for an object to be imaged. For example, the object to be imaged (e.g., object 1204) may have an irregular shape that switches between convex and concave at various portions. The regularly shaped footprint may have a smooth, continuous, convex shape that surrounds (e.g., completely surrounds) the irregular shape of the object to be imaged. The regularly shaped footprint, for example, may have the shape of an ellipsoid (e.g., a non-circular ellipsoid).

At 1304, at least some of the detector units of an imaging system are advanced to the regularly shaped footprint. In some embodiments, all of the detector units are advanced to the regularly shaped footprint. In other embodiments, some of the detector units may be advanced while others are left in a retracted position or position distant from the regularly shaped footprint. In some embodiments, a first group of detectors may be brought to the regularly shaped footprint and used to acquire imaging information while a second group of detectors is retracted, and, after the acquisition by the first group of detectors, the first group may be retracted and the second group advanced to the regularly shaped footprint, with the second group then used to acquire imaging information while the first group is retracted.

At 1306, imaging information is acquired with at least some of the detector units positioned at the regularly shaped footprint. In some embodiments, a first group of detectors may be brought to the regularly shaped footprint and used to acquire imaging information while a second group of detectors is retracted, and, after the acquisition by the first group of detectors, the first group may be retracted and the second group advanced to the regularly shaped footprint, with the second group then used to acquire imaging information while the first group is retracted. At 1308, an image is reconstructed using imaging information acquired at 1306.

Figure 14A:
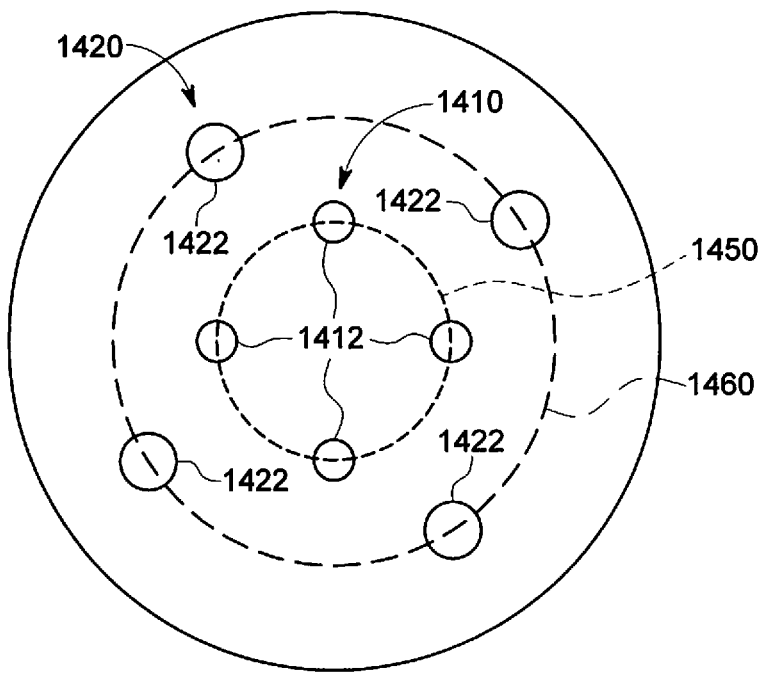
FIG. 14a depicts an imaging system with a first group of detectors advanced and a second group of detectors retracted, according to an embodiment.
Figure 14B:
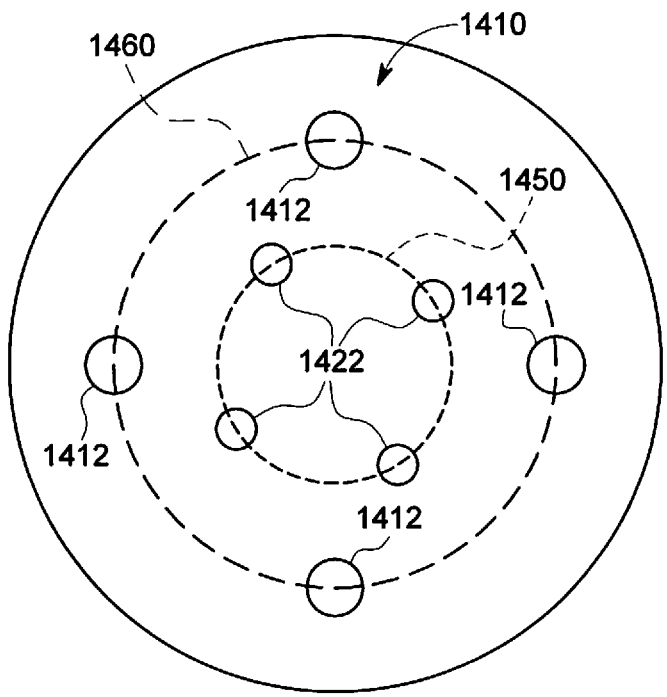
FIG. 14b depicts the imaging system of FIG. 14a with the second group of detectors advanced and the first group of detectors retracted.

Additionally or alternatively, in some embodiments, the processing unit 120 is configured to advance or position radially inwardly different groups of detectors at different times. FIGS. 14a and 14b depict an example imaging system 1400 with different groups of detectors advanced and retracted. As seen in FIG. 14a, a first group 1410 of detector units 1412 are at a radially inward position 1450, while a second group 1420 of detector units 1422 are at a radially outward position 1460. However, in the configuration shown in FIG. 14b, the first group 1410 of detector units 1412 are at the radially outward position 1460, while the second group 1420 of detector units 1422 are at the radially inward position 1450. In the configuration shown in FIG. 14a, the first group 1410 may be used to acquire imaging information proximate an object to be imaged, with the second group 1420 out of the way, while in the configuration shown in FIG. 14b, the second group 1420 may be used acquire imaging information proximate the object with first group 1410 out of the way. Accordingly, more detectors from various angles or views may be used proximate to an object than would be possible if only one group were positioned proximate to the object. For example, some objects may be small enough such that detectors would collide if all were attempted to be brought proximate to the object.

To achieve positioning such as that shown in FIGS. 14a and 14b, a processing unit (e.g., processing unit 120) may be configured to advance the first group 1410 of the detector units 1412 to the radially inward position 1450 while leaving the second group 1420 of the detector units 1422 at the radially outward position 1460. The processing unit may then control the imaging system 1400 to acquire imaging information with the first group 1410 of detector units 1412 at the radially inward position 1450. Next, the processing unit may retract the first group 1410 of detector units 1412 to the radially outward position 1460, and advance the second group 1420 of detector units 1422 to the radially inward position 1450. With the second group 1420 at the radially inward position 1450, additional imaging information may be acquired with the second group 1420 of detectors 1422. It may be noted that in some embodiments detectors at the radially outward position 1460 may be used to acquire imaging information, while in other embodiments, only detectors at the radially inward position 1450 may be utilized to acquire imaging information. It may further be noted that two groups of detectors are depicted in FIG. 14 for ease and clarity of illustration; however, in other embodiments more than two groups may be used. For example, three groups of detectors may be used, with two groups maintained at an outward position when the remaining group is at an inward position.

Figure 15:
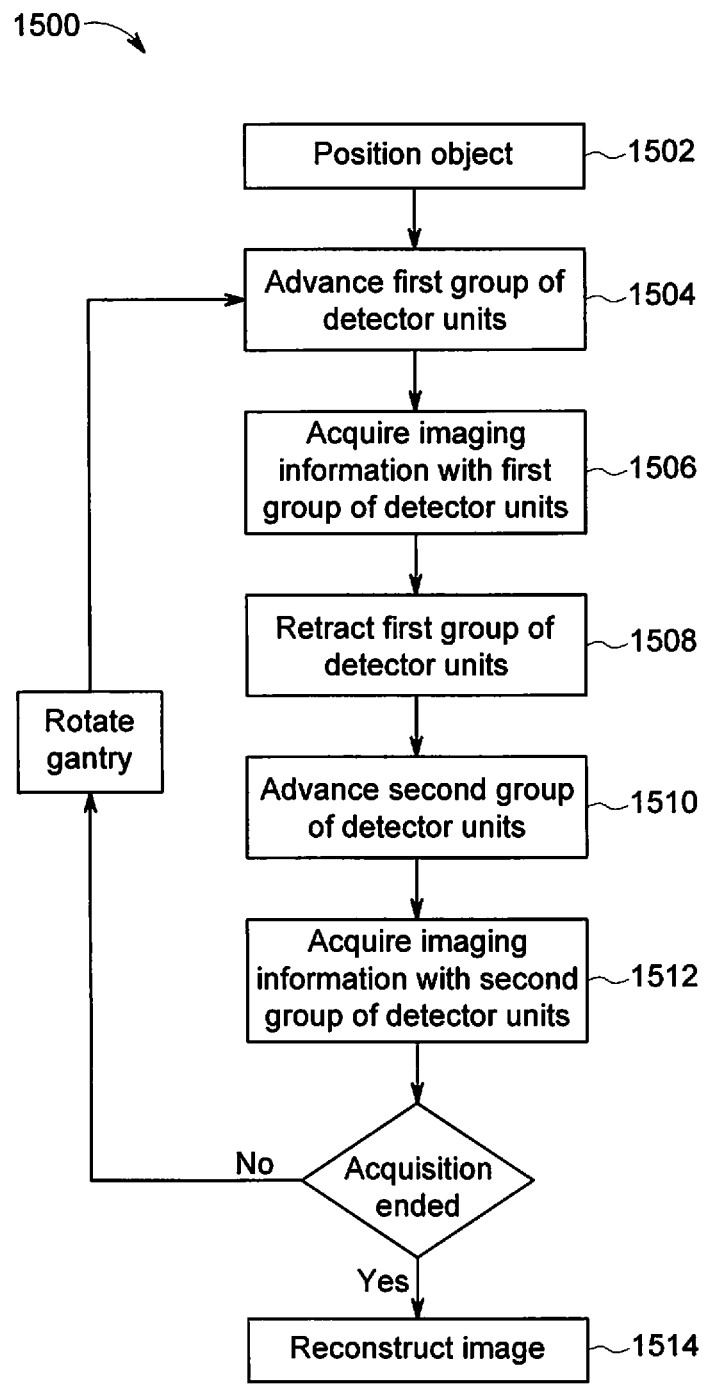
FIG. 15 shows a flowchart of a method, according to an embodiment.

FIG. 15 provides a flowchart of a method 1500 for controlling detector heads of a multi-head imaging system in accordance with various embodiments. The method 1500 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1500 may be able to be used as one or more algorithms to direct hardware (e.g., one or more aspects of the processing unit 120) to perform one or more operations described herein.

At 1502, an object to be imaged is positioned within the bore of a gantry (e.g., gantry 110). Plural detector units are disposed around the circumference of the bore. The detector units include detector heads that are articulable radially, such that the detector heads may be advanced radially toward the object to be imaged or retracted radially away from the object to be imaged.

At 1504, a first group of detector units is advanced to a radially inward position. While the first group is advanced, a second group of detector units is left at a radially outward position. (See, e.g., FIG. 14a.)

At 1506, imaging information is acquired with the first group of detector units at the first radially inward position. In some embodiments, imaging information is also acquired with the second group of detectors at the radially outward position, while in other embodiments information no imaging information is acquired with the second group of detectors at the radially outward position.

At 1508, the first group of detector units is retracted to the radially outward position, and, at 1510, the second group of detector units is advanced to the radially inward position. (See, e.g., FIG. 14b.)

At 1512, imaging information is acquired with the second group of detector units at the first radially inward position. In some embodiments, imaging information is also acquired with the first group of detectors at the radially outward position, while in other embodiments information no imaging information is acquired with the first group of detectors at the radially outward position.

At 1513, it is determined if the acquisition is ended (e.g., no more imaging information is to be acquired). If the acquisition is not ended, in the depicted embodiment, at 1515, the gantry may be rotated and the method 1500 return to 1504 for additional positioning of detector units and acquisition of imaging information. It may be noted that or more detector units may be retracted from a previous imaging position before rotating the gantry.

If the acquisition is ended, the method 1500 proceeds to 1514. At 1514, an image is reconstructed using the information acquired at 1506 and 1512.

Figure 16:
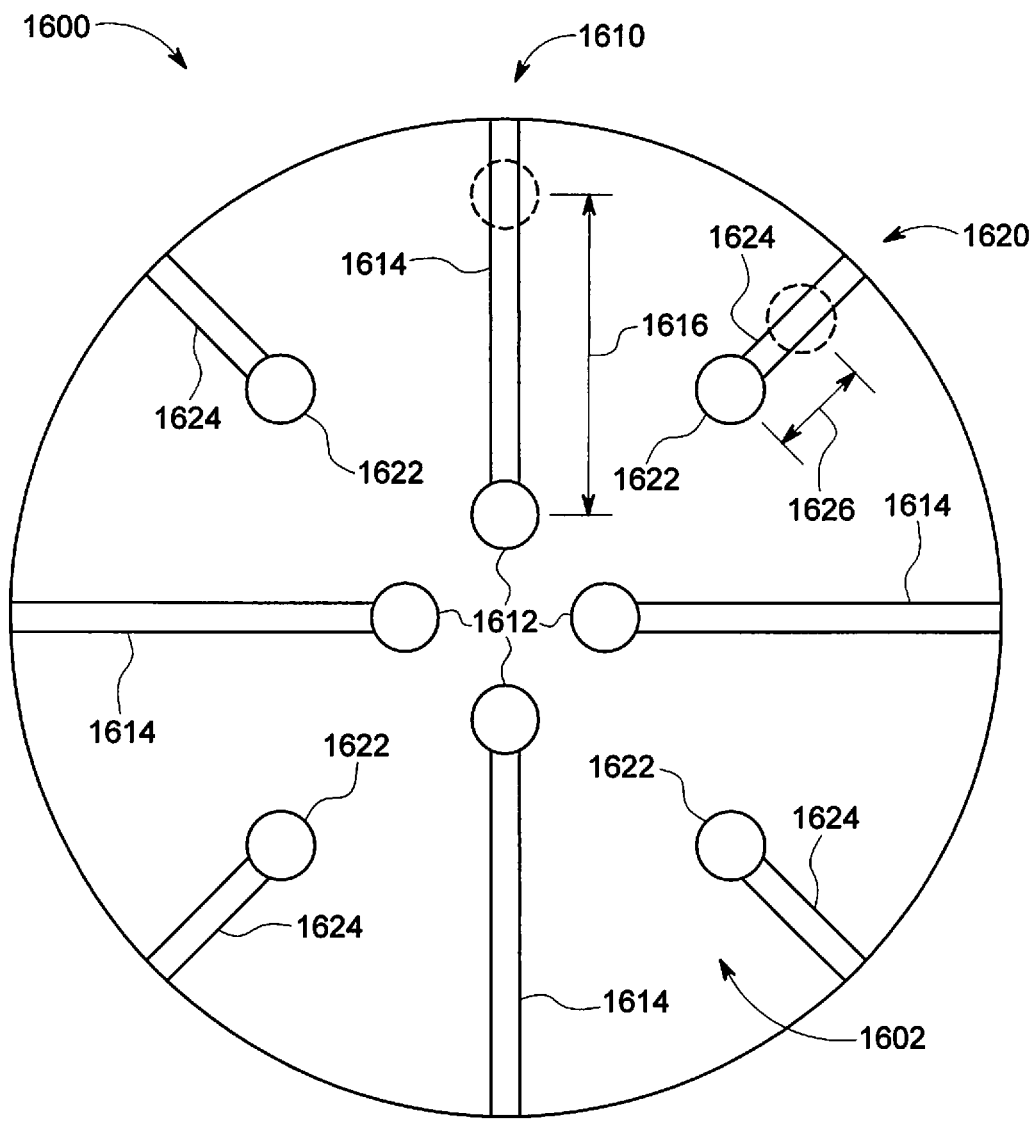
FIG. 16 depicts an imaging system in accordance with various embodiments.

It may be noted that in various embodiments, differently configured detector units may be used in conjunction with each other. For example, FIG. 16 provides a schematic view of an imaging system 1600. The imaging system 1600 may be generally similar in certain aspects to other imaging systems discussed herein. As seen in FIG. 16, the imaging system 1600 includes a first group 1610 of primary detector units 1612, and a second group 1620 of supplemental detector units 1622. In the illustrated example, the primary detector units 1612 and supplemental detector units 1622 are positioned alternately about the bore 1602.

The primary detector units 1612 each include an arm 1614 and include a range of motion 1616. The arms 1614 of the primary detector units 1612 may be extended or retracted (or otherwise articulated) to move the primary detector units 1612 radially toward or away from a bore 1602 of the imaging system 1600. Similarly, the supplemental detector units 1622 each include an arm 1624 and include a range of motion 1626. The arms 1624 of the supplemental detector units 1622 may be extended or retracted (or otherwise articulated) to move the supplemental detector units 1622 radially toward or away from a bore 1602 of the imaging system 1600. As seen in FIG. 16, the arms 1614 of the primary detector units 1612 are longer than the arms 1624 of the supplemental detector units 1622. Accordingly, the range of motion 1616 of the primary detector units 1612 is greater than the range of motion 1626 of the supplemental detector units, and the primary detector units 1612 are configured to advance further radially inwardly than the supplemental detector units 1622. Utilizing supplemental detector units with a lower range of motion 1626 in various embodiments lowers costs as well as avoids potential collisions of supplemental detector units with primary detector units if both are advanced too far radially inward. In some embodiments, the supplemental detector units 1622 may be fixed in position, or have no range of motion radially, to further reduce costs. Additionally, or alternatively, the supplemental detector units may be removable, and/or may be added only along a portion of the periphery of the bore 1602 (e.g., only along the upper half of the bore 1602) to further save space and/or cost.

Figure 18:
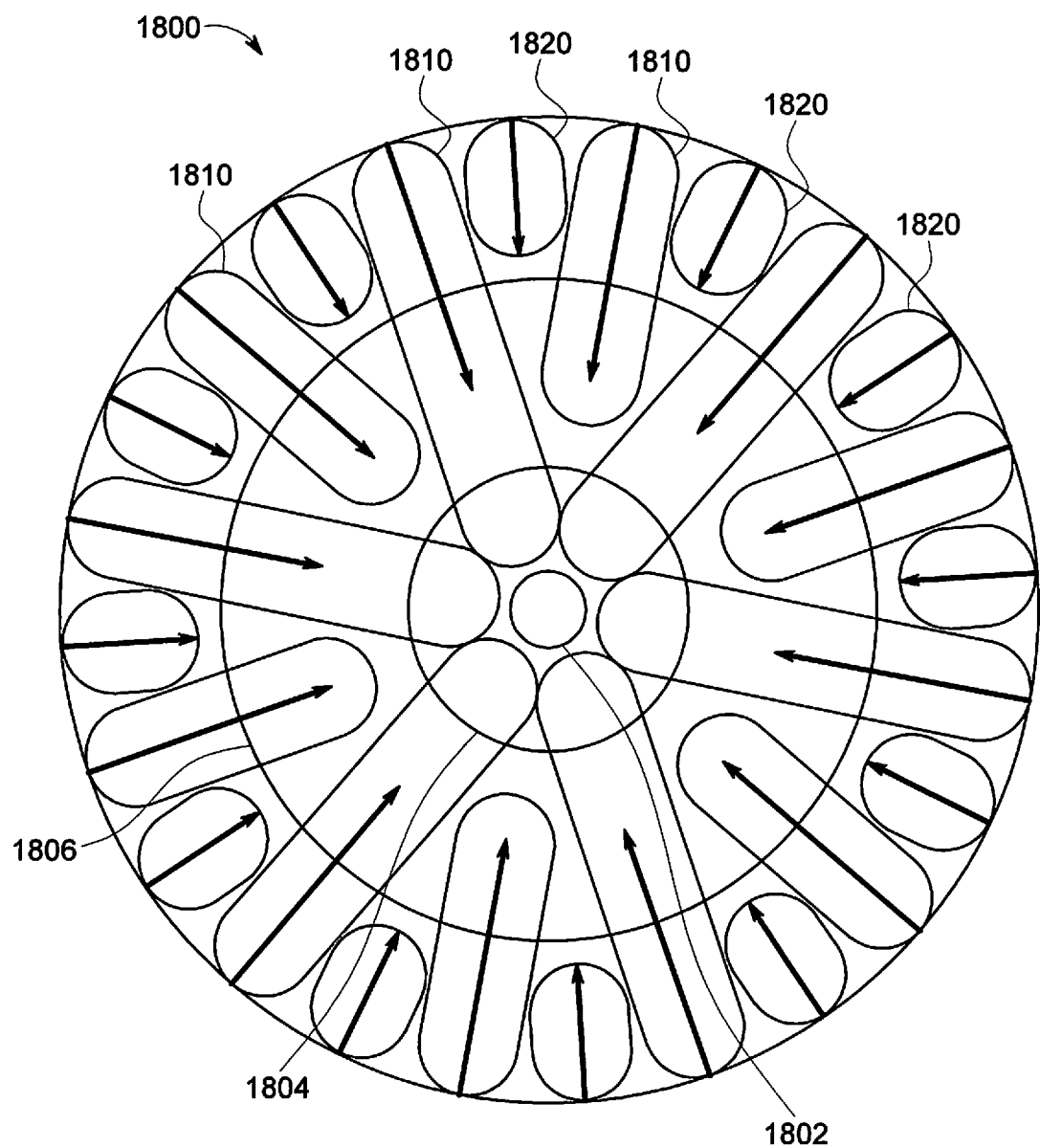
FIG. 18 provides a schematic view of an imaging system in accordance with various embodiments.

Accordingly, in various embodiments, additional detector arms may be added to an imaging system. The additional detector arms may be retracted, withdrawn, or otherwise positioned in a gantry between gaps of arms of primary detector units. For example, the additional detector arms may be used with obese patients or otherwise larger than normal objects to be imaged, and may have a limited radial motion. Shorter acquisition time and/or higher image quality may be obtained via the additional detector arms. In addition to FIG. 16, FIG. 18 provides an example of an imaging system with additional or supplemental arms. FIG. 18 provides a schematic view of an imaging system 1800.

As seen in FIG. 18, the system 1800 includes primary arms (or main arms) 1810, and supplemental arms (or additional arms) 1820. Outlines corresponding to three different sizes of objects are shown in FIG. 18—a smallest object 1802, a nominal object 1804, and a largest object 1806. The largest object 1806, for example, may correspond to an obese patient. The smallest object 1802, for example, may correspond to an infant, or, as another example, to a portion of an adult patient, such as a brain or limb.

In the illustrated embodiment, the main arms 1810 have an extended or full range of radial motion, while the supplemental arms 1820 have a reduced range of radial motion or no radial motion at all. For example, the main arms 1810 may be radially extendable to reach the smallest object 1802, while the supplemental arms may only be radially extendable to reach at or near the largest object 1806. As seen in FIG. 18, to image the smallest object 1802, every other main arm 1810 may be advanced to the outline corresponding to the smallest object 1802, while the remaining main arms remain at the outline corresponding to the nominal object 1804, and the supplemental arms remain at the outline corresponding to the largest object 1806 (or may be removed from the system 1800). To image the nominal object 1804, all of the main arms 1810 may be positioned at the outline corresponding to the nominal object 1804, the supplemental arms remain at the outline corresponding to the largest object 1806 (or may be removed from the system 1800). To image the largest object 1806, the main arms and the supplemental arms may be positioned at the outline corresponding to the largest object 1806.

Figure 17:
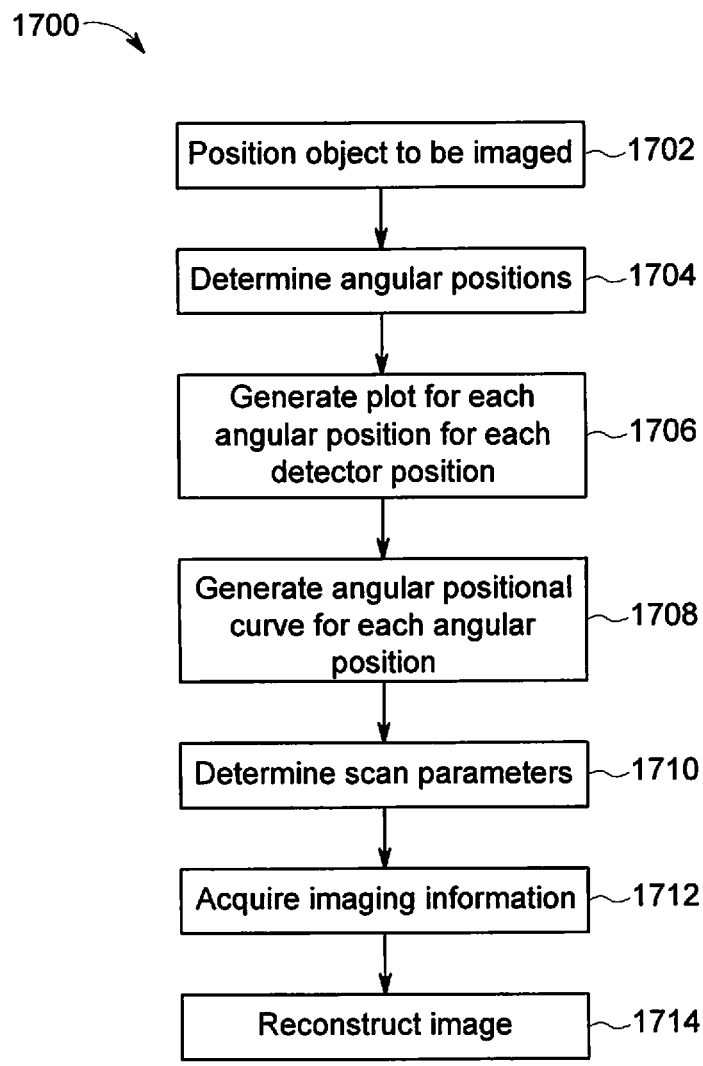
FIG. 17 shows a flowchart of a method, according to an embodiment.

FIG. 17 provides a flowchart of a method 1700 for controlling detector heads of a multi-head imaging system in accordance with various embodiments. The method 1700 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1700 may be able to be used as one or more algorithms to direct hardware (e.g., one or more aspects of the processing unit 120) to perform one or more operations described herein.

At 1702, an object to be imaged is positioned. The object, for example, may be a human patient (or portion thereof). In the depicted embodiment, the object is positioned within the bore of a gantry about which multiple detector units are positioned. Each detector unit is configured to pivot or sweep with respect to the object being imaged, such that the field of view of each detector unit is adjusted with respect to the object as the detector unit is swept. In various embodiments, the detector units may also rotate with the gantry, and/or be configured to be moved radially toward or away from the center of the bore.

At 1704, plural angular positions are determined. In the illustrated example, angular positions for each detector unit are determined along a corresponding sweep range for the given detector unit. The angular positions, for example, may be determined by using photon counts from an initial portion of a scan to determine boundaries or transitions (e.g., between air and soft tissue, between soft tissue and a volume of interest). The initial portion of the scan to acquire the initial imaging information may be performed after positioning the object in the gantry, with the initial imaging information used to determine the angular positions (which in turn are used to determine scan parameters for use in acquiring additional imaging information to be used to reconstruct a diagnostic image). It may be noted that in various embodiments the initial imaging information is not used to reconstruct an image before being used to determine the scan parameters as discussed herein. In some embodiments, four angular positions are determined: a first angular position corresponding to a transition from air to soft tissue in the field of view of the detector unit, a second angular position corresponding to a transition from soft tissue surrounding a volume of interest to the volume of interest (e.g., one or more particular organs), a third angular position corresponding to a transition from the field of interest to soft tissue, and a fourth angular position corresponding to a transition from soft tissue to air.

At 1706, a representation (e.g., a plot) is generated for each angular position for each detector unit position. At 1708, a model is generated (e.g., an angular positional curve is generated for each angular position using a plot generated at 1706). For an example of such a plot and angular positional curves, see FIG. 11 and related discussion.

At 1710, scan parameters are determined. The scan parameters are for use in performing a diagnostic scan of the object being imaged, and are determined using the model (e.g., angular positional curves) generated at 1708. Examples of scan parameters include, without limitation, sweep range, sweep speed, radial position, number of detector units to be used, and gantry rotational position. In some embodiments, scan parameters may be determined for a detector unit position that was not used to acquire initial imaging information for use in determining angular positions. For example, a detector unit may be idle during an initial imaging information acquisition but used for a subsequent diagnostic imaging acquisition. For instance, a first group of detectors at a radially inward position may be used to acquire initial imaging information for determining scan parameters for both the first group of detectors as well as a second group of detectors that are at a radially outward position during the initial acquisition, but are subsequently moved to the radially inward position for at least a portion of a diagnostic imaging acquisition.

As another example, scan parameters may be determined for at least one additional detector unit position corresponding to a rotation of the gantry. For instance, the at least one additional detector unit position may include a first additional detector unit position that is interposed between a first detector unit position of a first detector unit and a second detector unit position of a second detector unit, with at least one angular position for the first additional detector unit determined using the angular positional curve.

At 1712, imaging information is acquired using the determined scan parameters. For example, each detector unit may be used to acquire imaging information using a sweep range and one or more sweep speeds along the range determined at 1710. For example, in various embodiments where four angular positions are determined as discussed in the example described in connection with step 1704, each detector unit may be swept at a first, faster rate between the first angular position and the second angular position, swept at a second, slower rate between the second angular position and the third angular position, and swept at the first rate between the third angular position and fourth angular position. Accordingly, more time is spent relatively over the volume of interest than over soft tissue outside of the volume of interest, providing more efficient imaging by acquiring relatively more information of the volume of interest than would be acquired using a single, constant sweep rate between the first and fourth angular positions. It may be noted that, additionally or alternatively, imaging information may be acquired using one or more aspects of other methods discussed herein, such as method 1300 and/or method 1500.

At 1714, an image is reconstructed using the imaging information acquired at 1712. In some embodiments, initial imaging information used to determine the angular positions may also be used in conjunction with the imaging information acquire at 1712.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A method for use with a nuclear medicine (NM) multi-head imaging system comprising a plurality of detector units distributed about a gantry, where each of the plurality of detector units is configured to pivot to define a corresponding sweep range, the method comprising:
   determining plural angular positions along the corresponding sweep range for each of the plurality of detector units;
   identifying a detector unit position based on a location of the corresponding detector unit with respect to a bore of the gantry;
   generating a representation of the plural angular positions correlated to detector unit position for each of the plurality of detector units;
   generating a model based on the plural angular positions using the representation,
   wherein the model includes, for each angular position, an angular positional curve comprising points corresponding to the angular position of each detector unit position of the plurality of detector units, wherein the angular positional curve for each angular position includes points of corresponding detector unit positions for that particular angular position, whereby each angular positional curve includes points of multiple detector unit positions of the plurality of detector units for a respective angular position;
   determining scan parameters to be used to image an object using the model;
   acquiring imaging information using the determined scan parameters;
   reconstructing an image using the imaging information; and
   displaying the image on a display.

2. The method of claim 1, further comprising determining additional scan parameters for at least one additional detector unit position corresponding to a rotation of the gantry.

3. The method of claim 2, wherein the at least one additional detector unit position includes a first additional detector unit position that is interposed between a first detector unit position of a first detector unit and a second detector unit position of a second detector unit, and wherein the angular position for the first additional detector unit position is determined using the angular positional curve.

4. The method of claim 1, wherein acquiring the imaging information comprises:
   sweeping each detector unit at a first rate between a first angular position and a second angular position;
   sweeping each detector unit at a second rate between the second angular position and a third angular position; and
   sweeping each detector unit at a third rate between the third angular position and a fourth angular position, wherein both the first rate and the third rate are faster than the second rate.

5. The method of claim 4, wherein the second angular position is associated with a first boundary of a volume of interest and the third angular position is associated with a second boundary of the volume of interest.

6. The method of claim 4, wherein the first rate is the same as the third rate.

7. The method of claim 1, further comprising:
   advancing a first group of detector units to a first, radially inward position while leaving a second group of detector units at a second, radially outward position;
   acquiring first imaging information with the first group of detector units at the first, radially inward position;
   retracting the first group of detector units to the second, radially outward position;
   advancing the second group of detector units to the first, radially inward position; and
   acquiring additional imaging information with the second group of detector units at the first, radially inward position.

8. The method of claim 1, further comprising:
   determining a regularly shaped footprint that surrounds an irregular shape of the object to be imaged;
   advancing at least some of the plurality of detector units to the regularly shaped footprint; and
   acquiring imaging information with the at least some of the detector units positioned at the regularly shaped footprint.

9. The method of claim 1, wherein the plural angular positions for each detector unit include a first angular position corresponding to a first boundary between air and tissue, a second angular position corresponding to a first boundary between tissue and a volume of interest, a third angular position corresponding to a second boundary between the volume of interest and tissue, and a fourth angular position corresponding to a second boundary between tissue and air.

10. The method of claim 9, wherein acquiring the imaging information comprises:
   sweeping each detector unit at a first rate between the first angular position and the second angular position;
   sweeping each detector unit at a second rate between the second angular position and the third angular position, wherein the second rate is slower than the first rate; and
   sweeping each detector unit at the first rate between the third angular position and the fourth angular position.

11. The method of claim 1, wherein the plural angular positions correspond to boundaries of at least one of the object or a volume of interest.

12. The method of claim 11, wherein the plural angular positions are identified based on data acquired during one or more preliminary sweeps with each of the plurality of detector units.

13. A method for use with a nuclear medicine (NM) multi-head imaging system comprising a plurality of detector units distributed about a gantry, where each of the plurality of detector units is configured to pivot to define a corresponding sweep range, the method comprising:

determining plural angular positions along the corresponding sweep range for each of the plurality of detector units;

identifying a detector unit position based on a location of the corresponding detector unit with respect to a bore of the gantry;

generating a representation of the plural angular positions correlated to detector unit position for each of the plurality of detector units, wherein the representation correlates detector unit position along a first axis and points corresponding to each of the plural angular positions for each detector unit position of the plurality of detector units along a second axis perpendicular to the first axis;

generating a model based on the plural angular positions using the representation, wherein the model includes, for each angular position, an angular positional curve comprising points corresponding to the angular position of each detector unit position of the plurality of detector units, wherein the angular positional curve for each angular position includes points of corresponding detector unit positions for that particular angular position, whereby each angular positional curve includes points of multiple detector unit positions of the plurality of detector units for a respective angular position;

determining scan parameters to be used to image an object using the model;

acquiring imaging information using the determined scan parameters;

reconstructing an image using the imaging information; and displaying the image on a display.

14. A non-transitory computer readable storage medium including instructions that, when executed, cause one or more processors to perform the following:

determine plural angular positions along a corresponding sweep range for each of a plurality of detector units of a nuclear medicine (NM) multi-head imaging system, where each of the plurality of detector units is configured to pivot to define the corresponding sweep range;

identify a detector unit position based on a location of the corresponding detector unit with respect to a bore of the NM multi-head imaging system;

generate a representation of the plural angular positions correlated to detector unit position for each of the plurality of detector units, wherein the representation correlates detector unit position along a first axis and points corresponding to each of the plural angular positions for each detector unit position of the plurality of detector units along a second axis perpendicular to the first axis;

generate a model based on the plural angular positions using the representation, wherein the model includes, for each angular position, an angular positional curve comprising points corresponding to the angular position of each detector unit position of the plurality of detector units, wherein the angular positional curve for each angular position includes points of corresponding detector unit positions for that particular angular position, whereby each angular positional curve includes points of multiple detector unit positions of the plurality of detector units for a respective angular position;

determine scan parameters to be used to image an object using the model;

acquire imaging information using the determined scan parameters;

reconstruct an image using the imaging information; and display the image on a display.

15. The non-transitory computer readable storage medium of claim 14, wherein the plural angular positions correspond to boundaries of the object.

16. The non-transitory computer readable storage medium of claim 14, wherein the instructions, when executed, further cause the one or more processors to:

sweep each detector unit at a first rate between a first angular position and a second angular position;

sweep each detector unit at a second rate between the second angular position and a third angular position, wherein the first rate is faster than the second rate; and sweep each detector unit at the first rate between the third angular position and a fourth angular position.

17. The non-transitory computer readable storage medium of claim 14, wherein, when executed, further cause the one or more processors to identify the plural angular positions based on data acquired during one or more preliminary sweeps with each of the plurality of detector units.

* * * * *